US007846412B2

(12) United States Patent
Nie et al.

(10) Patent No.: US 7,846,412 B2
(45) Date of Patent: Dec. 7, 2010

(54) BIOCONJUGATED NANOSTRUCTURES, METHODS OF FABRICATION THEREOF, AND METHODS OF USE THEREOF

(75) Inventors: Shuming Nie, Atlanta, GA (US); Xiaohu Gao, Decatur, GA (US)

(73) Assignee: Emory University, Atlanta, GA (US)

( * ) Notice: Subject to any disclaimer, the term of this patent is extended or adjusted under 35 U.S.C. 154(b) by 673 days.

(21) Appl. No.: 10/988,923

(22) Filed: Nov. 15, 2004

(65) Prior Publication Data
US 2005/0136258 A1 Jun. 23, 2005

Related U.S. Application Data

(60) Provisional application No. 60/532,028, filed on Dec. 22, 2003.

(51) Int. Cl.
C01B 31/00 (2006.01)
H01L 21/00 (2006.01)
H01L 21/326 (2006.01)
H01L 21/469 (2006.01)
G01N 33/48 (2006.01)

(52) U.S. Cl. .......................... 423/414; 439/87; 438/52; 438/466; 438/780; 702/19; 702/20

(58) Field of Classification Search .................. None
See application file for complete search history.

(56) References Cited

U.S. PATENT DOCUMENTS 7,297,494 B2 11/2007 Bao et al.

OTHER PUBLICATIONS

Dubertret et al., Science, vol. 298, pp. 1759-1762, 2002.*
Savic et al., Science, vol. 300, pp. 615-618, Apr. 2003.*
Ludwigs et al., Nature Materials, vol. 2, pp. 744-747, Nov. 2003.*
Schulke et al., PNAS, vol. 100, pp. 12590-12595, 2003.*
Wu, et al.; Immunofluorescent labeling of cancer marker Her2 and other cellular targets with semiconductor quantum dots; Nature Biotechnology; vol. 21, Jan. 2003; pp. 41-46.
Chen, et al.; One-Step Synthesis of FePt Nanoparticles with Tunable Size; J. Am. Chem. Soc.; Received Apr. 23, 2004.
Sun, et al.; Controlled Synthesis and Assembly of FePt Nanoparticles; J. Phys. Chem; B; 2003, 107; pp. 5419-5425.
Jana, et al.; Size- and Shape-Controlled Magnetic (Cr, Mn, Fe, Co, Ni) Oxide Nanocrystals via a Simple and General Approach; Amer. Chem. Society; Received May 17, 2004.
Hyeon, et al.; Synthesis of Highly Crystalline and Monodisperse Maghemite Nanocrystallites without a Size-Selection Process; J. Am. Chem. Soc.; 2001, 123; pp. 12798-12801.
Nunez, et al.; Preparation, Characterization, and Magnetic Properties of Fe-Based Alloy Particles with Elongated Morphology; Chem. Mater; 2003, 15; pp. 3558-3563.
Sun, et al.; Monodisperse FePt Nanoparticles and Ferromagnetic FePt Nanocrystal Superlattices; Science; vol. 287; Mar. 17, 2000; pp. 1989-1992.
Sun, et al.; Monodispserse $Mfe_2O_4$ (M=Fe, Co, Mn) Nanoparticles; J. Am. Chem. Soc.; 2004, 126; pp. 273-279.
Jana, et al.; Single-Phase and Gram-Scale Routes toward Nearly Monodisperse Au and Other nOble metal Nanocrystals; J. Am. Chem. Soc.; 2003, 125; p. 14280-14281.
Chan, et al.; Luminescent quantum dots for multiplexed biological detection and imaging; Current Opinion in Biotechnology; Analytical biotechnology; 2002, 13; pp. 40-46.
Eisenstein; What Lies Beneath—Tracking Tumors with Quantum Dots; Nature.com website; Aug. 20, 2004.
Krieger; Quantum Dots Light Up Tumors; ScienceNOW website; http://sciiencenow.sciencemag.org/cgi/content/full/2004/720/3; Jul. 20, 2004.
Jain, et al.; Zooming in and out with quantum dots; Nature Biotechnology; vol. 22, No. 8; Aug. 2004; pp. 959-960.
Emory University Press Release, Jul. 27, 2004; Emory Scientists Target Tumors with Nanoparticle "Quantum Dots".
Henry; Targeting Cancer Cells; Chemical and Engineering News; Jul. 20, 2004, Biotechnology.
Wood; Nanoparticles seek out and destroy cancer; Materialstoday; Sep. 2004.
Ludwig, et al., "Self-assembly of Functional Nanostructures from ABC Triblock Copolymers," Nature Materials, vol. 2, pp. 744-747, Nov. 2003.
Dubertret, et al., In Vivo Imaging of Quantum Dots Encapsulated in Phospholipid Micelles,: Science, vol. 298 pp. 1759-1762, 2002.
Savic, et al., "Micellar Nanocontainers Distribute to Defined Cytoplasmic Organelles," Science, vol. 300, pp. 615-618, Apr. 2003.
Schulke, et al., "The homodimer of prostate-specific membrane antigen is a functional target for cancer therapy," PNAS, vol., No., pp. 12590-12595, 2003.
International Search Report and Written Opinion.

* cited by examiner

Primary Examiner—Shubo (Joe) Zhou
(74) Attorney, Agent, or Firm—Thomas, Kayden, Horstemeyer & Risley, LLP

(57) ABSTRACT

Nanostructures, methods of preparing nanostructures, methods of detecting targets in subjects, and methods of treating diseases in subjects, are disclosed. An embodiment, among others, of the nanostructure includes a quantum dot and a hydrophobic protection structure. The hydrophobic protection structure includes a capping ligand and an amphiphilic copolymer, where the hydrophobic protection structure encapsulates the quantum dot.

17 Claims, 9 Drawing Sheets

RED
DYE
RED
QD

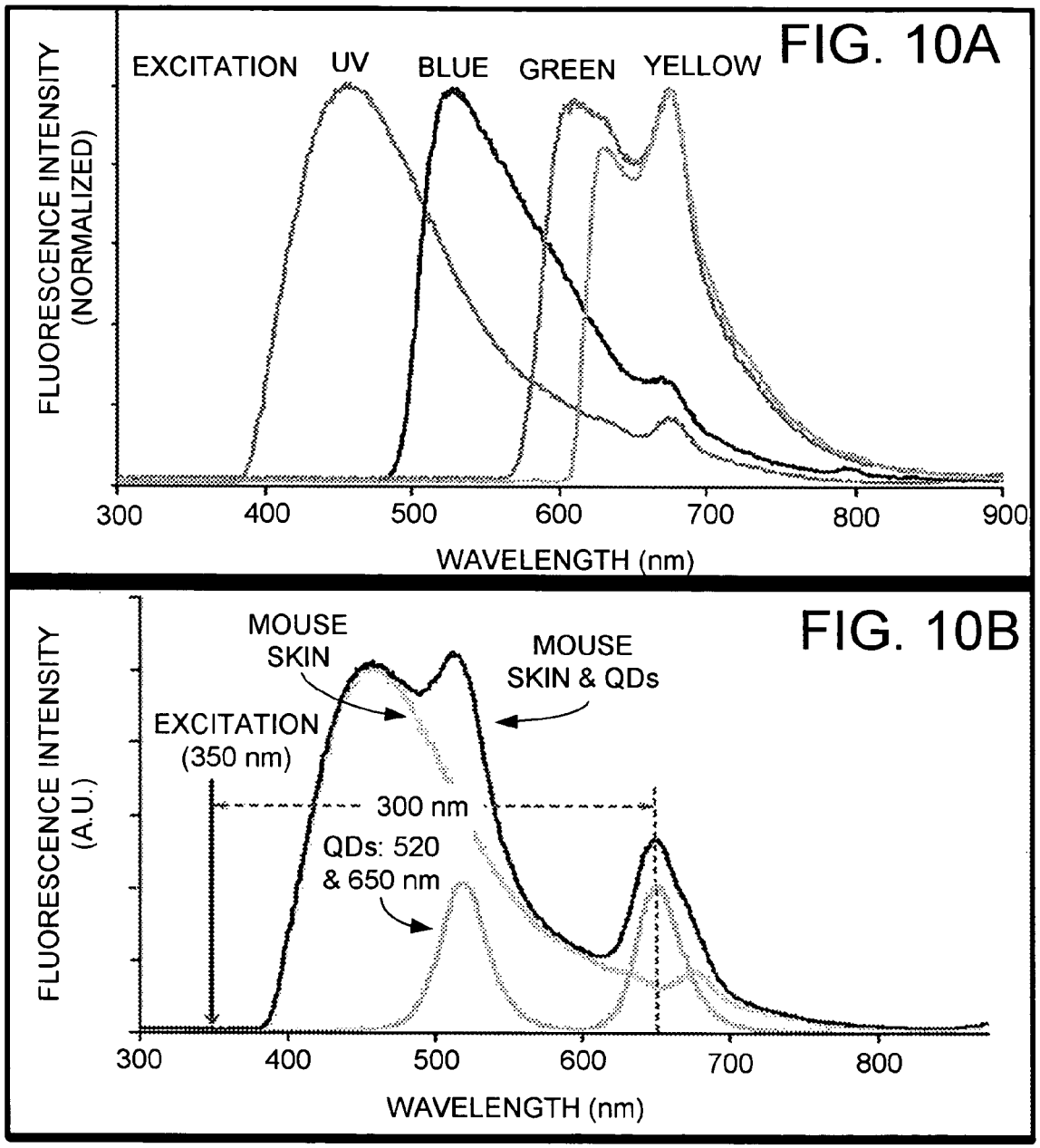

BIOCONJUGATED NANOSTRUCTURES, METHODS OF FABRICATION THEREOF, AND METHODS OF USE THEREOF

CROSS-REFERENCE TO RELATED APPLICATIONS

This application claims priority to U.S. Provisional Patent Application Ser. No. 60/532,028, entitled "BIOCONJUGATED NANOSTRUCTURES, METHODS OF FABRICATION THEREOF, AND METHODS OF USE THEREOF" filed on Dec. 22, 2003, the entirety of which is hereby incorporated by reference.

STATEMENT REGARDING FEDERALLY SPONSORED RESEARCH OR DEVELOPMENT

This invention was made with government support under Grant No.: R01 GM 60562 awarded by the National Institute of Health. The government has certain rights in the invention.

FIELD OF THE INVENTION(S)

The present disclosure relates generally to nanostructures, and relates more particularly, to bioconjugated nanostructures.

BACKGROUND

Recent advances have shown that nanometer-sized semiconductor particles can be covalently linked with biorecognition molecules such as peptides, antibodies, nucleic acids, or small-molecule ligands for applications as fluorescent probes. In comparison with organic fluorophores, these quantum-confined particles or quantum dots (QDs) exhibit unique optical and electronic properties, such as size- and composition-tunable fluorescence emission from visible to infrared wavelengths, large absorption coefficients across a wide spectral range, and very high levels of brightness and photostability. Due to their broad excitation profiles and narrow/symmetric emission spectra, high-quality QDs are also well suited for optical multiplexing, in which multiple colors and intensities are combined to encode genes, proteins, and small-molecule libraries.

Therefore, the development of high-sensitivity and high-specificity probes beyond the intrinsic limitations of organic dyes and fluorescent proteins is of considerable interest to many areas of research, ranging from molecular and cellular biology to molecular imaging and medical diagnostics.

SUMMARY

Briefly described, embodiments of this disclosure, among others, include nanostructures, methods of preparing nanostructures, methods of detecting targets in subjects, and methods of treating diseases in subjects. An embodiment, among others, of the nanostructure includes a quantum dot and a hydrophobic protection structure. The hydrophobic protection structure includes a capping ligand and an amphiphilic copolymer, where the hydrophobic protection structure encapsulates the quantum dot.

Another embodiment of the nanostructure includes at least one nanospecies and a hydrophobic protection structure. The hydrophobic protection structure includes at least one compound selected from a capping ligand, an amphiphilic copolymer, and combinations thereof, where the hydrophobic protection structure encapsulates the nanospecies.

An embodiment, among others, of the method of preparing one a nanostructure includes: providing a nanospecies; and forming a hydrophobic protection structure around the nanospecies that includes at least one compound selected from a capping ligand, an amphiphilic copolymer, and combinations thereof.

An embodiment, among others, of the method of detecting a target in a subject includes: providing one of the nanostructures described above having a bio-compatibility compound disposed substantially on the surface of the hydrophobic protection structure, and at least one probe disposed substantially on the surface of the hydrophobic protection structure, wherein a first probe has an affinity for the target; introducing the nanostructure to a subject; and determining the presence of the target in the subject corresponding to the probe by detecting the nanospecies.

An embodiment, among others, of the method of treating a disease in a subject includes providing one of the nanostructures described above having a bio-compatibility compound disposed substantially on the surface of the hydrophobic protection structure, and at least one probe disposed substantially on the surface of the hydrophobic protection structure, wherein a first probe has an affinity of the target; introducing the nanostructure to the subject in need of treatment of the disease.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 6A is the original image; FIG. 6B is an unmixed autofluorescence image; FIG. 6C is an unmixed QD image; and FIG. 6D is a super-imposed image. After in vivo imaging, histological and immunocytochemical examinations confirmed that the QD signals came from an underlying tumor.

FIG. 9A illustrates an image that was obtained with blue excitation at 470 nm and 515 nm long-pass emission, and FIG. 9B illustrates an image that was obtained with yellow excitation at 570 nm and 600 nm long-pass emission. Cancer cells (MDA-MB-231) were labeled with either Tat-QD or Tat-nanobeads (250-nm particles with embedded organic dyes, $\lambda_{ex}$=575, and $\lambda_{em}$=615 nm, Sigma-Aldrich, St Louis, Mo.) in cell culture. Prior to injection, the QD- and dye-labeled cells were similarly bright when examined with an epi-fluorescence microscope. Approximately 1000 cells were injected subcutaneously into a living mouse at two adjacent sites for in vivo imaging.

FIG. 10A illustrates a graph depicting autofluorescence spectra of a nude mouse skin specimen obtained at four excitation wavelengths ($\lambda$=350, 480, 535 and 560 nm). Note the presence of significant autofluorescence up to 800-850 nm and a background peak at about 670 nm. FIG. 10B illustrates a comparison of mouse skin and QD emission spectra obtained under the same excitation conditions, demonstrating that the QD signals can be shifted to a spectral region where the autofluorescence is reduced.

DETAILED DESCRIPTION

Figure 1:
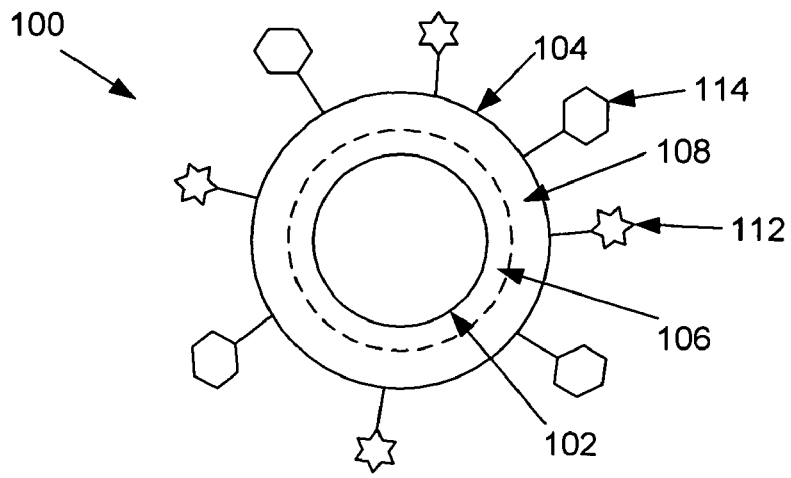
FIG. 1 illustrates an exemplar embodiment of a nanostructure.

In accordance with the purpose(s) of the present disclosure, as embodied and broadly described herein, embodiments of the present disclosure, in one aspect, relate to bioconjugated nanostructures (hereinafter nanostructures), methods of fabricating these nanostructures, and methods of using these nanostructures. The nanostructures are distinguishable and can be individually detected. In this regard, the nanostructures can be modified so that the nanostructures interact with certain target molecules, which allow detection of the target molecules (e.g., in-vivo) thereby determining the area in which the target molecules are located, for example.

The nanostructures can be used in many areas such as, but not limited to, biomolecule array systems, biosensing, biolabeling, gene expression studies, protein studies, medical diagnostics, diagnostic libraries, microfluidic systems, delivery vehicles, cosmetics, detergents, and nanoparticle-polymer arrays (e.g., self-assembly, lithography and patterning). In particular, the nanostructures can be used in in-vivo diagnostic and/or therapeutic applications such as, but not limited to, targeting and/or imaging of diseases and/or conditions (e.g., identify the type of disease, locate the proximal locations of the disease, and deliver drugs to the diseased cells (e.g., cancer cells) in living animals, as described in detail Example 1. The nanostructures in combination with spectral imaging can be used for multiplexed imaging and detection of genes, proteins, and the like, in single living cells.

Embodiments of the nanostructure include, but are not limited to, a nanospecies (e.g., quantum dots, metal particles and metal oxide particles) and a hydrophobic protection structure that encapsulates the nanospecies. In addition, the nanostructure can include, but is not limited to, a bio-compatibility compound (e.g., polyethylene glycol (MW about 500 to 50,000 and 1000 to 10,000), dextran, and derivatives such as amino-dextran and carboxy-dextran, and polysaccharides) and a probe (e.g., polynucleotide, polypeptide, a therapeutic agent, and/or a drug). The bio-compatibility compound and/or the probe are substantially disposed (e.g., attached to the surface of the hydrophobic protection structure and/or attached within the hydrophobic protection structure) on the hydrophobic protection structure. The hydrophobic protection structure includes a capping ligand and/or a amphiphilic copolymer (e.g., amphiphilic block copolymers, amphiphilic random copolymers, amphiphilic alternating copolymers, amphiphilic periodic copolymers, and combinations thereof).

In another embodiment, the nanostructure can include two or more nanospecies or two of more types of nanospecies. In addition, the nanostructure can include a hydrophobic protection structure having two or more copolymers (e.g., two or more block copolymers). Further, the nanostructure can include multiple nanospecies and multiple copolymers (e.g., block copolymers). In addition, the nanostructure can include two or more different types of probes having different functions. Furthermore, the nanospecies and the copolymers (e.g., block copolymers) can be assembled into micro and macro structures.

In still another embodiment, the nanostructure can be included in a porous material such as, but is not limited to, a mesoporous material (e.g., a pore diameter of about 1 to 100 nanometers (nm)), a macroporous material (e.g., a pore diameter of greater than about 100 nm), and a hybrid mesoporous/macroporous material. The porous material can be made of a material such as, but not limited to, a polymer, a copolymer, a metal, a silica material, cellulose, ceramic, zeolite, and combinations thereof. The preferred porous materials are silica materials and polystyrene and polystyrene co-polymers (e.g., divinylbenzene, methacrylic acid, maleic acid). The shape of the porous material can be, but is not limited to, spherical, cubic, monolith (i.e., bulk material), two dimensional and three dimensional arrays. The preferred shape of the porous material is spherical (e.g., silica beads and polymer beads (e.g., chromatographic beads), ceramic, and molecular sieves).

FIG. 1 illustrates an exemplar embodiment of the nanostructure 100. The nanostructure includes, but is not limited to, a nanospecies 102 having a hydrophobic protection structure 104 that encapsulates the nanospecies 102. In addition, the nanostructure 100 can include, but is not limited to, a bio-compatibility compound 112 and a probe 114. The hydrophobic protection structure 104 includes a capping ligand layer 106 and/or a copolymer layer 108 (e.g., amphiphilic block copolymer). The following illustrative examples will use amphiphilic block copolymers, but other copolymers such as, but not limited to, amphiphilic random copolymers, amphiphilic alternating copolymers, amphiphilic periodic copolymers, and combinations thereof, can be used in combination with block copolymers, as well as individually or in any combination. In addition, the term "amphiphilic block copolymer" will be termed "block copolymer" hereinafter.

Figure 2A:
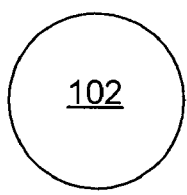
FIGS. 2A through 2D illustrates an exemplary method of forming the nanostructure illustrated in FIG. 1.
Figure 2B:
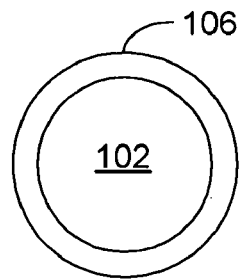
Figure 2C:
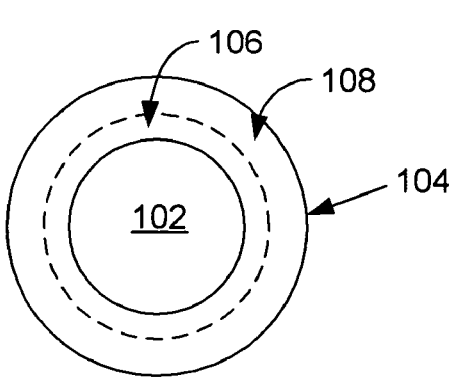
Figure 2D:
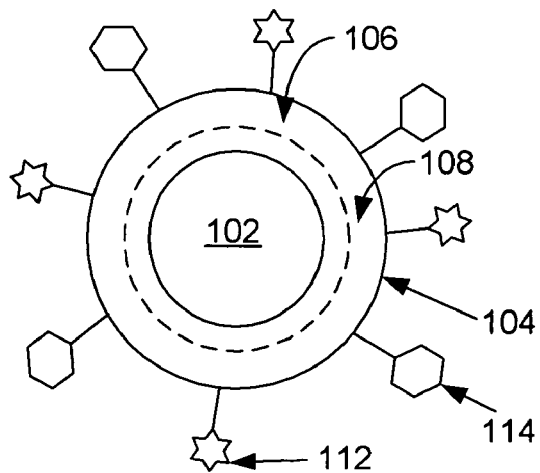

In general, the nanostructure 100 can be formed in a manner described in FIGS. 2A through 2D. FIG. 2A illustrates the nanospecies 102, while FIG. 2B illustrates the capping ligand 106 disposed on the nanospecies 102. FIG. 2C illustrates the block copolymer disposed on the capping ligand layer 106 to form the hydrophobic protection structure 104. FIG. 2D illustrates the addition of the bio-compatibility compound 112 and the probe 114 onto the hydrophobic protection structure 104.

As mentioned above, the nanostructure can include a number of types of nanospecies such as, but not limited to, semiconductor, metal, and metal oxide nanoparticles (e.g., gold, silver, copper, titanium, nickel, platinum, palladium, oxides thereof (e.g., $Cr_2O_3$, $CO_3O_4$, NiO, MnO, $CoFe_2O_4$, and $MnFeO_4$), and alloys thereof), metalloid and metalloid oxide nanoparticles, the lanthanide series metal nanoparticles, and combinations thereof. In particular, semiconductor quantum dots are described in more detail below and in U.S. Pat. No. 6,468,808 and International Patent Application WO 03/003015, which are incorporated herein by reference. Furthermore, the magnetic nanoparticles (e.g., those having magnetic or paramagnetic properties) can include, but are not limited to, iron nanoparticles and iron composite nanoparticles (e.g., $Fe_2O_3$, $Fe_3O_4$, FePt, FeCo, FeAl, FeCoAl, $CoFe_2O_4$, and $MnFeO_4$).

As indicated above, the nanostructure can include quantum dots such as, but not limited to, luminescent semiconductor quantum dots. In general, quantum dots include a core and a cap, however, uncapped quantum dots can be used as well. The "core" is a nanometer-sized semiconductor. While any core of the IIA-VIA, IIIA-VA or IVA-IVA, IVA-VIA semiconductors can be used in the context of the present disclosure, the core must be such that, upon combination with a cap, a luminescent quantum dot results. A IIA-VIA semiconductor is a compound that contains at least one element from Group IIB and at least one element from Group VIA of the periodic table, and so on. The core can include two or more elements. In one embodiment, the core is a IIA-VIA, IIIA-VA or IVA-IVA semiconductor that ranges in size from about 1 nm to about 20 nm. In another embodiment, the core is more preferably a IIA-VIA semiconductor and ranges in size from about 2 nm to about 10 nm. For example, the core can be CdS, CdSe, CdTe, ZnSe, ZnS, PbS, PbSe or an alloy.

The "cap" is a semiconductor that differs from the semiconductor of the core and binds to the core, thereby forming a surface layer on the core. The cap can be such that, upon combination with a given semiconductor core a luminescent quantum dot results. The cap should passivate the core by having a higher band gap than the core. In one embodiment, the cap is a IIA-VIA semiconductor of high band gap. For example, the cap can be ZnS or CdS. Combinations of the core and cap can include, but are not limited to, the cap is ZnS when the core is CdSe or CdS, and the cap is CdS when the core is CdSe. Other exemplary quantum dots include, but are not limited to, CdS, ZnSe, CdSe, CdTe, $CdSe_xTe_{1-x}$, InAs, InP, PbTe, PbSe, PbS, HgS, HgSe, HgTe, CdHgTe, and GaAs.

The wavelength emitted (i.e., color) by the quantum dots can be selected according to the physical properties of the quantum dots, such as the size and the material of the nanocrystal. Quantum dots are known to emit light from about 300 nanometers (nm) to 1700 nm (e.g., UV, near IR, and IR). The colors of the quantum dots include, but are not limited to, red, blue, green, and combinations thereof. The color or the fluorescence emission wavelength can be tuned continuously. The wavelength band of light emitted by the quantum dot is determined by either the size of the core or the size of the core and cap, depending on the materials which make up the core and cap. The emission wavelength band can be tuned by varying the composition and the size of the QD and/or adding one or more caps around the core in the form of concentric shells.

The intensity of the color of the quantum dots can be controlled. For each color, the use of 10 intensity levels (0, 1, 2, ... 9) gives 9 unique codes ($10^1-1$), because level "0" cannot be differentiated from the background. The number of codes increase exponentially for each intensity and each color used. For example, a three color and 10 intensity scheme yields 999 ($10^3-1$) codes, while a six color and 10 intensity scheme has a theoretical coding capacity of about 1 million ($10^6-1$). In general, n intensity levels with m colors generate ($n^m-1$) unique codes. Use of the intensity of the quantum dots has applications in nanostructures including a plurality of different types of quantum dots having different intensity levels and also in nanostructures including a plurality of different types of quantum dots having different intensity levels that are included in a porous material. The quantum dots are capable of absorbing energy from, for example, an electromagnetic radiation source (of either broad or narrow bandwidth), and are capable of emitting detectable electromagnetic radiation at a narrow wavelength band when excited. The quantum dots can emit radiation within a narrow wavelength band (FWHM, full width at half maximum) of about 40 nm or less, thus permitting the simultaneous use of a plurality of differently colored quantum dots with little or no spectral overlap.

The synthesis of quantum dots is well known and is described in U.S. Pat. Nos. 5,906,670; 5,888,885; 5,229,320; 5,482,890; 6,468,808; 6,306,736; 6,225,198, etc., International Patent Application WO 03/003015, (all of which are incorporated herein by reference) and in many research articles. The wavelengths emitted by quantum dots and other physical and chemical characteristics have been described in U.S. Pat. No. 6,468,808 and International Patent Application WO 03/003015 and will not be described in any further detail. In addition, methods of preparation of quantum dots are described in U.S. Pat. No. 6,468,808 and International Patent Application WO 03/003015 and will not be described any further detail.

As mentioned above, the hydrophobic protection structure includes the capping ligand and/or the block copolymer. In particular, when the nanospecies is a quantum dot, the hydrophobic protection layer includes the capping ligand and the block copolymer, where the capping ligand and the block copolymer interact with one another to form the hydrophobic protection structure. As such, the capping ligand and the block copolymer are selected to form an appropriate hydrophobic protection structure. For example, the block copolymer and the nanospecies can interact through interactions such as, but not limited to, hydrophobic interactions, hydrophilic interactions, pi-stacking, etc., depending on the surface coating of the nanospecies and the molecular structure of polymers. Additional details regarding the capping ligand and the block copolymer are provided in Example 1 below.

The capping ligand caps the nanospecies (e.g., quantum dot) and forms a layer on the nanospecies, which subsequently bonds with the block copolymer to form the hydrophobic protection structure. The capping ligand can include compounds such as, but not limited to, an O=PR$_3$ compound, an O=PHR$_2$ compound, an O=PHR$_1$ compound, a H$_2$NR compound, a HNR$_2$ compound, a NR$_3$ compound, a HSR compound, a SR$_2$ compound, and combinations thereof. "R" can be a C$_1$ to C$_{18}$ hydrocarbon, such as but not limited to, linear hydrocarbons, branched hydrocarbons, cyclic hydrocarbons, substituted hydrocarbons (e.g., halogenated), saturated hydrocarbons, unsaturated hydrocarbons, and combinations thereof. Preferably, the hydrocarbon is a saturated linear C$_4$ to C$_{18}$ hydrocarbon, a saturated linear C$_6$ to C$_{18}$ hydrocarbon, and a saturated linear C$_{18}$ hydrocarbon. A combination of R groups can be attached to P, N, or S. In particular, the chemical can be selected from tri-octylphosphine oxide, stearic acid, and octyldecyl amine.

As mentioned above, the copolymer includes, but is not limited to, amphiphilic block copolymers, amphiphilic random copolymers, amphiphilic alternating copolymers, amphiphilic periodic copolymers, and combinations thereof. The amphiphilic random copolymer can include, but is not limited to random copolymer poly(methyl acrylate-co-acrylic acid); random copolymer poly(methyl methacrylate-co-n-butyl acrylate); random copolymer poly(methyl methacrylate-co-hydroxypropyl acrylate); random copolymer poly(styrene-co-p-carboxyl chloro styrene); random copolymer poly(styrene-co-4-hydroxystyrene); random copolymer poly(styrene-co-4-vinyl benzoic acid); random copolymer poly(styrene-co-4-vinyl pyridine); (and combinations thereof. The amphiphilic alternating copolymer can include, but is not limited to, poly(maleic anhydride-alt-1-octadecene), poly(maleic anhydride-alt-1-tetradecene), alternating copolymer poly(carbo tert.butoxy α-methyl styrene-alt-maleic anhydride) and alternating copolymer poly(carbo tert.butoxy norbornene-alt-maleic anhydride), and combinations thereof.

The block copolymer includes amphiphilic di- and or triblock copolymers. In addition, the copolymer can include hydrocarbon side chains such as, but not limited to, 1-18-carbon aliphatic side chains, 1-18-carbon alkyl side chains, and combinations thereof. Furthermore, the di or tri block copolymers have at least one hydrophobic block and at least one hydrophilic block.

The following is in an exemplary list of amphiphilic random and alternating copolymers: random copolymer poly(dimethyl siloxane-co-diphenyl siloxane); random copolymer poly(methyl acrylate-co-acrylic acid); random copolymer poly(methyl methacrylate-co-n-butyl acrylate); random copolymer poly(methyl methacrylate-co-t-butyl acrylate); random copolymer poly(methyl methacrylate-co-hydroxypropyl acrylate); random copolymer poly(tetrahydrofuranyl methacrylate-co-ethyl methacrylate); random copolymer poly(styrene-co-4-bromostyrene); random copolymer poly(styrene-co-butadiene); random copolymer poly(styrene-co-diphenyl ethylene); random copolymer poly(styrene-co-t-butyl methacrylate); random copolymer poly(styrene-co-t-butyl-4-vinyl benzoate); random copolymer poly(styrene-co-p-carboxyl chloro styrene); random copolymer poly(styrene-co-p-chloromethyl styrene); random copolymer poly(styrene-co-methyl methacrylate); random copolymer poly(styrene-co-4-hydroxystyrene); random copolymer poly(styrene-co-4-vinyl benzoic acid); random copolymer poly(styrene-co-4-vinyl pyridine); alternating copolymer poly(carbo tert.butoxy α-methyl styrene-alt-maleic anhydride); alternating copolymer poly(carbo tert.butoxy norbornene-alt-maleic anhydride); alternating copolymer poly(α-methyl styrene-alt-methyl methacrylate); and alternating copolymer poly(styrene-alt-methyl methacrylate).

The following in an exemplary list of amphiphilic copolymers: poly((meth)acrylic acid) based copolymers (e.g., poly (acrylic acid-b-methyl methacrylate); poly(methyl methacrylate-b-acrylic acid); poly(methyl methacrylate-b-sodium acrylate); poly(sodium acrylate-b-methyl methacrylate); poly(methacrylic acid-b-neopentyl methacrylate); poly(neopentyl methacrylate-b-methacrylic acid); poly(t-butyl methacrylate-b-ethylene oxide); poly(methyl methacrylate-b-sodium methacrylate); and poly(methyl methacrylate-b-N,N-dimethyl acrylamide)), polydiene and hydrogenated polydiene based copolymers (e.g., poly(butadiene(1,2 addition)-b-methylacrylic acid; poly(butadiene(1,4 addition)-b-acrylic acid); poly(butadiene(1,4 addition)-b-sodium acrylate); poly(butadiene(1,4 addition)-b-ethylene oxide; poly (butadiene(1,2 addition)-b-ethylene oxide); poly(butadiene (1,2 addition)-b-ethylene oxide)-hydroxy benzoic ester terminal group; 4-methoxy benzyolester terminated poly (butadiene-b-ethylene oxide) diblock copolymer; poly(butadiene-b-N-methyl 4-vinyl pyridinium iodide); poly(isoprene-b-N-methyl 2-vinyl pyridinium iodide); poly (isoprene-b-ethylene oxide) (1,4 addition); poly(isoprene-b-ethylene oxide) (1,2 and 3,4 addition); poly(propylene-ethylene-b-ethylene oxide); and hydrogonated poly (isoprene-b-ethylene oxide) (1,2 addition)), hydrogentated diene based copolymers (e.g., poly(ethylene-b-ethylene oxide) and poly(isoprene-b-ethylene oxide)), poly(ethylene oxide) based copolymers (e.g., poly(ethylene oxide-b-acrylic acid); poly(ethylene oxide-b-∈-caprolactone); poly(ethylene oxide-b-6-(4'-cyanobiphenyl-4-yloxy)hexyl methacrylate); poly(ethylene oxide-b-lactide); poly(ethylene oxide-b-2-hydroxyethyl methacrylate); poly(ethylene oxide-b-methyl methacrylate); poly(-methyl methacrylate-b-ethylene oxide); poly(ethylene oxide-b-methacrylic acid); poly(ethylene oxide-b-2-methyl oxazoline); poly(ethylene oxide-b-propylene oxide); poly(ethylene oxide-b-t-butyl acrylate); poly (ethylene oxide-b-tetrahydrofurfuryl methacrylate); and poly (ethylene oxide-b-N,N-dimethylethylmethacrylate)), polyisobutylene based copolymers (e.g., poly(isobutylene-b-ethylene oxide)), polystyrene based copolymers (e.g., poly (styrene-b-acrylic acid); poly(styrene-b-sodium acrylate); poly(styrene-b-acrylamide); poly(p-chloromethyl styrene-b-acrylamide); poly(styrene-co-p-chloromethyl styrene-b-acrylamide); poly(styrene-co-p-chloromethyl styrene-b-acrylic acid); poly(styrene-b-cesium acrylate); poly(styrene-b-ethylene oxide); poly(4-styrenesulfonic acid-b-ethylene oxide); poly(styrene-b-methacrylic acid); poly(styrene-b-sodium methacrylate); poly(styrene-b-N-methyl 2-vinyl pyridinium iodide); and poly(styrene-b-N-methyl-4-vinyl pyridinium iodide)), polysiloxane based copolymers (e.g., poly (dimethylsiloxane-b-acrylic acid)), poly(2-vinyl naphthalene) based copolymers (e.g., poly(2-vinyl naphthalene-b-acrylic acid)), poly (vinyl pyridine and N-methyl vinyl pyridinium iodide) based copolymers (e.g., poly(2-vinyl pyridine-b-ethylene oxide); poly(N-methyl 2-vinyl pyridinium iodide-b-ethylene oxide); and poly(N-methyl 4-vinyl pyridinium iodide-b-methyl methacrylate)).

The following in an exemplary list of amphiphilic diblock copolymers: poly(meth)acrylate based copolymers (e.g., poly(n-butyl acrylate-b-methyl methacrylate); poly(n-butyl acrylate-b-dimethylsiloxane-co-diphenyl siloxane); poly(t-butyl acrylate-b-methyl methacrylate); poly(t-butyl acrylate-b-4-vinylpyridine); poly(2-ethyl hexyl acrylate-b-4-vinyl pyridine); poly(t-butyl methacrylate-b-2-vinyl pyridine); poly(2-hydroxyl ethyl acrylate-b-neopentyl acrylate); poly (2-hydroxyl ethyl methacrylate-b-neopentyl methacrylate); poly(2-hydroxyl ethyl methacrylate-b-n-butyl methacrylate); poly(2-hydroxyl ethyl methacrylate-b-t-butyl methacrylate); poly(methyl methacrylate-b-acrylonitrile); poly(methyl methacrylate-b-t-butyl methacrylate); poly(isotactic methyl methacrylate-b-syndiotactic methyl methacrylate); poly(m-ethyl methacrylate-b-t-butyl acrylate); poly(methyl methacrylate-b-trifluroethyl methacrylate); poly(methyl methacrylate-b-2-hydroxyethyl methacrylate with cholesteryl chloroformate); poly(methyl methacrylate-b-disperse red 1 acrylate); poly(methyl methacrylate-b-2-hydroxyethyl methacrylate); poly(methyl methacrylate-b-neopentyl acrylate); and poly(methacrylate-b-2-pyranoxy ethyl methacrylate)), polydiene based copolymers (e.g., poly(butadiene(1,2 addition)-b-i-butyl methacrylate); poly(butadiene(1,2 addition)-b-s-butyl methacrylate); poly(butadiene(1,4 addition)-b-t-butyl acrylate; poly(butadiene(1,2 addition)-b-t-butyl acrylate; poly(butadiene(1,2 addition)-b-t-butyl methacrylate); poly(butadiene(1,4 addition)-b-∈-caprolactone); poly (butadiene((1,4 addition)-b-dimethylsiloxane); poly(butadiene(1,4 addition)-b-methyl methacrylate) (syndiotactic); poly(butadiene(1,2 addition)-b-methyl methacrylate); poly (butadiene(1,4 addition)-b-4-vinyl pyridine; poly(isoprene (1,4 addition)-b-methyl methacrylate(syndiotactic)); poly (isoprene(1,4 addition)-b-2-vinyl pyridine; poly(isoprene (1,2 addition)-b-4-vinyl pyridine); and poly(isoprene(1,4 addition)-b-4-vinyl pyridine)), polyisobutylene based copolymers (e.g., poly(isobutylene-b-t-butyl methacrylate); poly(isobutylene-b-∈-caprolactone); poly(isobutylene-b-dimethylsiloxane); poly(isobutylene-b-methyl methacrylate); poly(isobutylene-b-4-vinyl pyridine), polystyrene based copolymers (e.g., poly(styrene-b-n-butyl acrylate); poly(styrene-b-t-butyl acrylate); poly(styrene-b-t-butyl acrylate), broad distribution; poly(styrene-b-disperse red 1 acrylate); poly(p-chloromethyl styrene-b-t-butyl acrylate); poly (styrene-b-N-isopropyl acrylamide); poly(styrene-b-n-butyl methacrylate); poly(styrene-b-t-butyl methacrylate); poly (styrene-b-cyclohexyl methacrylate); poly(styrene-b-2-cholesteryloxycarbonyloxy ethyl methacrylate); poly(styrene-b-N,N-dimethyl amino ethyl methacrylate); poly(styrene-b-ethyl methacrylate); poly(styrene-b-2-hydroxyethyl methacrylate); poly(styrene-b-2-hydroxypropyl methacrylate); poly(styrene-b-methyl methacrylate); poly(styrene-b-methylmethacrylate); poly(styrene-b-n-propyl methacrylate); poly(styrene-b-butadiene(1,4 addition)); poly(styrene-b-butadiene(1,2 addition)); poly(styrene-b-isoprene(1,4 addition)); poly(styrene-b-isoprene(1,2 addition or 3,4 addition)); poly(styrene-b-isoprene(1,4 addition)), hydrogenated; tapered block copolymer poly(styrene-b-butadiene); tapered block copolymer poly(styrene-b-ethylene); poly(styrene-b-∈-caprolactone); poly(styrene-b-1-lactide); poly(styrene-b-dimethylsiloxane), trimethylsilane endgroup; poly(styrene-b-dimethylsiloxane), silanol endgroup; poly(styrene-b-methyl phenyl siloxane); poly(styrene-b-ferrocenyldimethylsilane); poly(styrene-b-t-butyl styrene); poly(styrene-b-t-butoxystyrene); poly(styrene-b-4-hydroxyl styrene); poly(4-amino benzyl-b-styrene); poly(styrene-b-2-vinyl pyridine); poly(styrene-b-4-vinyl pyridine); and poly (α-methylstyrene-b-4-vinyl pyridine), poly(vinyl naphthalene) based copolymers (e.g., poly(2-vinyl naphthalene-b-n-butyl acrylate), poly(2-vinyl naphthalene-b-t-butyl acrylate); poly(2-vinyl naphthalene-b-methyl methacrylate); and poly (2-vinyl naphthalene-b-dimethylsiloxane)), poly(vinyl pyridine) based copolymers (e.g., poly(2-vinyl pyridine-b-∈-caprolactone); poly(2-vinyl pyridine-b-methyl methacrylate); and poly(4-vinyl pyridine-b-methyl methacrylate)), poly (propylene oxide-b-∈-caprolactone) (e.g., poly (propylene oxide-b-F-caprolactone)), polysiloxane based copolymers (e.g., poly(dimethylsiloxane-b-n-butyl acrylate); poly(dimethylsiloxane-b-t-butyl acrylate); poly(dimethylsiloxane-b-t-butyl methacrylate); poly(dimethylsiloxane-b-∈-caprolactone); poly(dimethylsiloxane-b-6-(4'-cyanobiphenyl-4-yloxy)hexyl methacrylate); poly(dimethylsiloxane-b-1-ethoxy ethyl methacrylate); poly(dimethylsiloxane-b-hydroxy ethyl acrylate); and poly(dimethylsiloxane-b-methyl methacrylate)), adipic anhydride based copolymers (e.g., poly(ethylene oxide-b-adipic anhydride); poly(propylene oxide-b-adipic anhydride); poly(dimethyl siloxane-b-adipic anhydride); poly(methyl methacrylate-b-adipic anhydride); and poly(2-vinyl pyridine-b-adipic anhydride)).

The following in an exemplary list of amphiphilic a-b-a triblock copolymers: poly((meth)acrylate) based triblock copolymers (e.g., poly(n-butyl acrylate-b-9,9-di-n-hexyl-2,7-fluorene-b-n-butyl acrylate); poly(t-butyl acrylate-b-9,9-di-n-hexyl-2,7-fluorene-b-t-butyl acrylate); poly(acrylic acid-b-9,9-di-n-hexyl-2,7-fluorene-b-acrylic acid); poly(t-butyl acrylate-b-methyl methacrylate-b-t-butyl acrylate); poly(t-butyl acrylate-b-styrene-b-t-butyl acrylate); poly(m-ethyl methacrylate-b-butadiene(1,4 addition)-b-methyl methacrylate); poly(methyl methacrylate-b-n-butyl acrylate-b-methyl methacrylate); poly(methyl methacrylate-b-t-butyl acrylate-b-methyl methacrylate); poly(methyl methacrylate-b-t-butyl methacrylate acid-b-methyl methacrylate); poly(m-ethyl methacrylate-b-methacrylic acid-b-methyl methacrylate); poly(methyl methacrylate-b-dimethylsiloxane-b-methyl methacrylate); poly(methyl methacrylate-b-9,9-di-n-hexyl-2,7-fluorene-b-methyl methacrylate); poly(methyl methacrylate-b-styrene-b-methyl methacrylate); poly(trimethylamonium iodide ethyl methacrylate-b-9,9-di-n-hexyl-2,7-fluorene-b-trimethylamonium iodide ethyl methacrylate); poly(N,N-dimethyl amino ethyl methacrylate-b-9,9-di-n-hexyl-2,7-fluorene-b-N,N-dimethyl amino ethyl methacrylate); and poly(N,N-dimethyl amino ethyl methacrylate-b-propylene oxide-b-N,N-dimethyl amino ethyl methacrylate)), polybutadiene based triblock copolymers (e.g., poly(butadiene(1,4 addition)-b-styrene-b-butadiene (1,4 addition))), poly(oxirane) based triblock copolymers (e.g., poly(ethylene oxide-b-9,9-di-n-hexyl-2,7-fluorene-b-ethylene oxide); poly(ethylene oxide-b-propylene oxide-b-ethylene oxide); poly(ethylene oxide-b-styrene-b-ethylene oxide); and poly(propylene oxide-b-dimethyl siloxane-b-propylene oxide)), polylactone and polylactide diblock copolymers (e.g., poly(lactide-b-ethylene oxide-b-lactide); poly(caprolactone-b-ethylene oxide-b-caprolactone); and alpha,-ω diacrylonyl terminated poly(lactide-b-ethylene oxide-b-lactide)), polyoxazoline based triblock copolymers (e.g., poly(2-methyl oxazoline-b-dimethyl siloxane-b-2-methyl oxazoline))), polystyrene based triblock copolymers (e.g., poly(styrene-b-acrylic acid-b-styrene); poly(styrene-b-butadiene (1,4 addition)-b-styrene); poly(styrene-b-butadiene (1,2 addition)-b-styrene); poly(styrene-b-butylene-b-styrene); poly(styrene-b-n-butyl acrylate-b-styrene); poly(styrene-b-t-butyl acrylate-b-styrene); poly(styrene-b-9,9-di-n-hexyl-2,7-fluorene-b-styrene); poly(styrene-b-ethyl acrylate-b-styrene); poly(styrene-b-isoprene-b-styrene); poly(styrene-b-ethylene oxide-b-styrene); poly(styrene-b-4-vinyl pyridine-b-styrene); and poly(styrene-b-dimethyl siloxane-b-styrene)), poly(vinyl pyridine) based triblock copolymers (e.g., poly(2-vinyl pyridine-b-butadiene(1,2 addition)-b-2-vinyl pyridine); poly(2-vinyl pyridine-b-styrene-b-2-vinyl pyridine); and poly(4-vinyl pyridine-b-styrene-b-4-vinyl pyridine).

The following in an exemplary list of amphiphilic a-b-c triblock copolymers: poly(styrene-b-butadiene-b-methyl methacrylate) (e.g., poly(styrene-b-butadiene-b-methyl methacrylate)), poly(styrene-b-butadiene-b-2-vinyl pyridine) (e.g., poly(styrene-b-butadiene-b-2-vinyl pyridine)), poly(styrene-b-t-butyl acrylate-b-methyl methacrylate) (e.g., poly(styrene-b-t-butyl acrylate-b-methyl methacrylate)), poly(styrene-b-isoprene-b-glycidyl methacrylate) (e.g., poly (styrene-b-isoprene-b-glycidyl methacrylate)), poly(styrene-b-2-vinyl pyridine-b-ethylene oxide) (e.g., poly(styrene-b-2-vinyl pyridine-b-ethylene oxide)), poly(styrene-b-anthracene methyl methacrylate-b-methymethacrylate) (e.g., poly(styrene-b-anthracene methyl methacrylate-b-methymethacrylate)), poly(styrene-b-t-butyl acrylate-b-2-vinyl pyridine) (e.g., poly(styrene-b-t-butyl acrylate-b-2-vinyl pyridine)), and poly(styrene-b-t-butyl methacrylate-b-2-vinyl pyridine) (e.g., poly(styrene-b-t-butyl methacrylate-b-2-vinyl pyridine)).

The following in an exemplary list of amphiphilic functionalized diblock and triblock copolymers: amino terminated poly(dimethylsiloxane-b-diphenylsiloxane); amino terminated poly(styrene-b-isoprene); amino terminated poly (ethylene oxide-b-lactone); hydroxy terminated poly(styrene-b-2-vinyl pyridine); hydroxy terminated polystyrene-b-poly(methyl methacrylate); α-hydroxy terminated poly (styrene-b-butadiene(1,2-addition)); 4-methoxy benzyolester terminated poly(butadiene-b-ethylene oxide) diblock copolymer; succinic acid terminated poly(butadiene-b-ethylene oxide) diblock copolymer; α,ω-disuccinimidyl succinate terminated poly(ethylene oxide-propylene oxide-ethylene oxide); cabinol at the junction of poly(styrene-b-isoprene(1,4 addition)); and silane at the junction of poly (styrene-b-2-vinyl pyridine).

In addition, the following is an exemplary list of amphiphilic block copolymers: poly(1-vinylpyrrolidone-co-vinyl acetate); poly(ethylene-co-propylene-co-5-methylene-2-norbornene); poly(styrene-co-acrylonitrile); poly(2-vinylpyridine-co-styrene); poly(ethylene-co-methacrylic acid) sodium salt; poly(acrylonitrile-co-butadiene-co-styrene); poly(vinyl chloride-co-vinyl acetate-co-maleic acid); poly (ethylene-co-vinyl acetate); poly(ethylene-co-ethyl acrylate); poly(4-vinylpyridine-co-styrene); poly(vinyl butyral-co-vinyl alcohol-co-vinyl acetate); poly(methyl methacrylate co-methacrylic acid); poly-(vinyl chloride-co-vinyl acetate-co-hydroxypropyl acrylate); Luviquat®HM 552; poly(vinyl chloride-co-vinyl acetate-co-vinyl alcohol); poly(styrene-co-divinylbenzene); poly(DL-lactide-co-glycolide); poly(acrylonitrile-co-methyl acrylate); poly[(vinyl chloride-co-(1-methyl-4-vinylpiperazine)]; poly(2-isopropenyl-2-oxazoline-co-methyl methacrylate); poly(tetrafluoroethylene oxide-co-difluoromethylene oxide) α,ω-diol, ethoxylated; poly [dimethylsiloxane-co-methyl(3-hydroxypropyl)siloxane]-graft-poly(ethylene glycol) methyl ether; poly(acrylonitrile-co-methacrylonitrile); poly(ethylene-co-1-butene); poly (vinylidene fluoride co-hexafluoropropylene); poly (ethylene-co-1-octene); poly(ethylene-co-methyl acrylate); poly(acrylonitrile-co-butadiene), amine terminated; poly (perfluoropropylene oxide-co-perfluoroformaldehyde); poly (butyl methacrylate-co-isobutyl methacrylate); poly(styrene-co-maleic anhydride), partial isooctyl ester, cumene terminated; poly(acrylonitrile-co-butadiene-co-acrylic acid), dicarboxy terminated; poly(vinyl alcohol-co-ethylene); poly (dimethylsiloxane-co-methylphenylsiloxane); poly(styrene-co-maleic anhydride); poly(Bisphenol A-co-epichlorohydrin); poly(styrene-co-butadiene); poly[(R)-3-hydroxybutyric acid-co-(R)-3-hydroxyvaleric acid]; poly (vinyl alcohol-co-vinyl acetate-co-itaconic acid); poly (methylstyrene-co-indene), hydrogenated; poly(4-vinylphenol-co-2-hydroxyethyl methacrylate); poly(styrene-co-maleic anhydride), cumene terminated; poly(methyl methacrylate-co-ethylene glycol dimethacrylate); poly(ethylene-co-propylene); poly(styrene-co-maleic acid), partial isobutyl/methyl mixed ester; poly(Bisphenol A-co-epichlorohydrin), glycidyl end-capped; poly(methyl methacrylate-co-methacrylic acid); poly(2-acrylamido-2-methyl-1-propanesulfonic acid-co-acrylonitrile); poly(propylene-co-tetrafluoroethylene); poly(butyl methacrylate-co-methyl methacrylate); poly(dimethylsiloxane-co-alkylmethylsiloxane); poly(acrylic acid-co-acrylamide) potassium salt; poly (oxymethylene-co-1,3-dioxepane); poly(chlorotrifluoroethylene-co-vinylidene fluoride); poly(melamine-co-formaldehyde), acrylated solution; poly(pentafluorostyrene-co-glycidyl methacrylate); poly(1,1,1,3,3,3-hexafluoroisopropyl methacrylate-co-glycidyl methacrylate); poly(2,2,3,4,4,4,-hexafluorobutyl methacrylate-co-glycidyl methacrylate); poly(2,2,3,3,3-pentafluoropropyl methacrylate-co-glycidyl methacrylate); poly[(propylmethacryl-heptaisobutyl-PSS)-co-(n-butylmethacrylate)]; poly(pyromellitic dianhydride-co-4,4'-oxydianiline), amic acid solution; poly(tert-butyl methacrylate-co-glycidyl methacrylate); poly[(propylmethacryl-heptaisobutyl-PSS)-co-hydroxyethylmethacrylate]; poly[(m-phenylenevinylene)-co-(2,5-dioctoxy-p-phenylenevinylene)]; poly [(methylmethacrylate)-co-(9-anthracenylmethyl methacrylate)]; poly[(methylmethacrylate)-co-(2-naphthylacrylate)]; poly[methylmethacrylate-co-(7-(4-trifluoromethyl)coumarin methacrylamide)]; poly[(methylmethacrylate)-co-(9-anthracenylmethyl acrylate)]; poly [(methylmethacrylate)-co-(9H-carbazole-9-ethylmethacrylate)]; poly[(propylmethacryl-heptaisobutyl-PSS)-co-(methylmethacrylate)]; poly[(isobutylene-alt-maleic acid), ammonium salt)-co-(isobutylene-alt-maleic anhydride)]; poly(ethylenecarbonyl-co-propylenecarbonyl); poly[4,5-difluoro-2,2-bis(trifluoromethyl)-1,3-dioxole-co-tetrafluoroethylene]; poly(dimethylsiloxane-co-diphenylsiloxane), trimethylsilyl terminated; poly(dimethylsiloxane-co-methylhydrosiloxane), trimethylsilyl terminated; poly (dimethylsiloxane-co-diphenylsiloxane), divinyl terminated; poly(styrene-co-methyl methacrylate); poly(styrene-co-α-methylstyrene); poly(1,4-cyclohexanedimethylene terephthalate-co-ethylene terephthalate); Amberjet™ 4200; poly [dimethylsiloxane-co-methyl(3-hydroxypropyl)siloxane]-graft-poly(ethylene glycol) [3-(trimethylammonio)propyl chloride]ether solution; poly[dimethylsiloxane-co-methyl(3-hydroxypropyl)siloxane]-graft-poly(ethylene/propylene glycol); poly(ethylene-co-butyl acrylate); poly(ethylene-co-ethyl acrylate-co-maleic anhydride); poly(ethyl methacrylate-co-methyl acrylate); poly(ethylene-co-1-butene-co-1-hexene); poly(melamine-co-formaldehyde), isobutylated solution; poly[Bisphenol A carbonate-co-4,4'-(3,3,5-trimethylcyclohexylidene) diphenol carbonate]; poly (acrylamide-co-acrylic acid); poly(styrene-co-maleic acid), partial sec-butyl/methyl mixed ester; poly(4-hydroxybenzoic acid-co-6-hydroxy-2-naphthoic acid); poly[butylene terephthalate-co-poly(alkylene glycol) terephthalate]; poly(ethylene-co-vinyl acetate-co-methacrylic acid); poly(melamine-co-formaldehyde), methylated; poly(acrylonitrile-co-butadiene), dicarboxy terminated; poly(vinyl chloride-co-vinyl acetate-co-2-hydroxypropyl acrylate); poly(tetrafluoroethylene oxide-co-difluoromethylene oxide) α,ω-diol; poly(melamine-co-formaldehyde), butylated solution; poly[(phenyl glycidyl ether)-co-formaldehyde]; poly(acrylamide-co-diallyldimethylammonium chloride) solution; poly(tetrafluoroethylene-co-perfluoro(propylvinyl ether)); poly(4-vinylpyridine-co-butyl methacrylate); poly(dimer acid-co-alkyl polyamine); poly(1-vinylpyrrolidone-co-2-dimethylaminoethyl methacrylate), quaternized solution; poly(methyl methacrylate-co-ethyl acrylate); Luviquat® FC 550; poly(vinyltoluene-co-α-methylstyrene); poly(epichlorohydrin-co-ethylene oxide-co-allyl glycidyl ether); poly(dimethylsiloxane-co-methylhydrosiloxane); polybutadiene-graft-poly(methyl acrylate-co-acrylonitrile); poly(styrene-co-maleic anhydride), partial 2-butoxyethyl ester, cumene terminated; poly(dimethylamine-co-epichlorohydrin) solution; poly(ethylene-co-acrylic acid); poly(acrylamide-co-acrylic acid) partial sodium salt; poly(hexafluoropropylene oxide-co-difluoromethylene oxide) monoalkylamide; poly(1-vinylpyrrolidone-co-2-dimethylaminoethyl methacrylate) solution; poly(acrylic acid-co-maleic acid) sodium salt; poly(ethylene-co-acrylic acid, zinc salt); poly(ethylene-co-tetrafluoroethylene); poly(2,2,2-trifluoroethyl methacrylate-co-glycidyl methacrylate); poly(pentabromophenyl acrylate-co-glycidyl methacrylate); poly(2,2,3,3,4,4,4-heptafluorobutyl methacrylate-co-glycidyl methacrylate; poly[methylmethacrylate-co-(disperse yellow 7 methacrylate)]; poly(2,2,3,3-tetrafluoropropyl methacrylate-co-glycidyl methacrylate); poly(pentabromophenyl methacrylate-co-glycidylmethacrylate); poly[methylmethacrylate-co-(Disperse Orange 3 methacrylamide)]; poly[((S)-( )-1-(4-nitrophenyl)-2-pyrrolidinemethyl)acrylate-co-methylmethacrylate]; poly[(methylmethacrylate)-co-(Disperse Red 13 methacrylate)]; poly[(methylmethacrylate)-co-(Disperse Red 13 acrylate)]; poly[methylmethacrylate-co-(N-(1-naphthyl)-N-phenylacrylamide)]; poly[(propylmethacryl-heptaisobutyl-PSS)-co-styrene]; poly(pyromellitic dianhydride-co-thionin); poly(ethylene glycol)-co-4-benzyloxybenzyl alcohol, polymer-bound; poly[(isobutylene-alt-maleimide)-co-(isobutylene-alt-maleic anhydride)]; poly[dimethylsiloxane-co-(3-aminopropyl)methylsiloxane]; poly[dimethylsiloxane-co-[3-(2-(2-hydroxyethoxy)ethoxy)propyl)methylsiloxane]; poly(vinylidene chloride-co-acrylonitrile-co-methyl methacrylate); poly(ethylene-co-1,2-butylene) diol; poly(DL-lactide-co-caprolactone) (40:60); poly(methyl methacrylate-co-butyl methacrylate); poly(tetrafluoroethylene oxide-co-difluoromethylene oxide)α,ω-diol bis(2,3-dihydroxypropyl ether); poly[dimethylsiloxane-co-(2-(3,4-epoxycyclohexyl)ethyl)methylsiloxane]; poly(vinyl chloride-co-isobutyl vinyl ether); poly(indene-co-coumarone); poly(styrene-co-4-bromostyrene-co-divinylbenzene); poly(ethylene-co-butyl acrylate-co-carbon monoxide); poly(vinyl acetate-co-butyl maleate-co-isobornyl acrylate) solution; poly(3,3',4,4'-benzophenonetetracarboxylic dianhydride-co-4,4'-oxydianiline/1,3-phenylenediamine), amic acid (solution); poly(tetrafluoroethylene-co-vinylidene fluoride-co-propylene); poly(ethylene-co-methacrylic acid) lithium salt; poly(styrene-co-butadiene-co-methyl methacrylate); poly(vinylidene chloride-co-vinyl chloride); poly(styrene-co-maleic acid), partial isobutyl ester; poly[4,4'-methylenebis(phenyl isocyanate)-alt-1,4-butanediol/poly(ethylene glycol-co-propylene glycol/polycaprolactone]; poly(ethylene-co-methacrylic acid); poly(isobutylene-co-maleic acid) sodium salt; poly(ethylene-co-methacrylic acid) zinc salt; poly(4-styrenesulfonic acid-co-maleic acid) sodium salt; poly(acrylonitrile-co-butadiene-co-acrylic acid), glycidyl methacrylate diester; poly(urea-co-formaldehyde), butylated solution; poly(ethylene-co-methyl acrylate-co-glycidyl methacrylate); poly[(phenyl glycidyl ether)-co-dicyclopentadiene]; poly[(o-cresyl glycidyl ether)-co-formaldehyde]; poly(urea-co-formaldehyde), methylated; poly(acrylic acid-co-maleic acid) solution; poly(3-hydroxybutyric acid-co-3-hydroxyvaleric acid); poly(p-toluenesulfonamide-co-formaldehyde); poly(styrene-co-allyl alcohol); poly(2-acrylamido-2-methyl-1-propanesulfonic acid-co-styrene); poly(acrylonitrile-co-butadiene); poly(4-vinylphenol-co-methyl methacrylate); poly[dimethylsiloxane-co-methyl(3-hydroxypropyl)siloxane]-graft-poly(ethylene-ran-propylene glycol) methyl ether; poly(hexafluoropropylene oxide-co-difluoromethylene oxide) monoamidosilane; poly(dimethylamine-co-epichlorohydrin-co-ethylenediamine) solution; poly(ethylene-co-butyl acrylate-co-maleic anhydride); poly(trimellitic anhydride chloride-co-4,4'-methylenedianiline); poly[methylmethacrylate-co-(Disperse Orange 3 acrylamide)]; poly[((S)-( )-1-(4-Nitrophenyl)-2-pyrrolidinemethyl)methacrylate-co-methylmethacrylate]; poly[(propylmethacryl-heptaisobutyl-PSS)-co-(t-butylmethacrylate)]; poly[(methylmethacrylate)-co-(2-naphthylmethacrylate)]; poly[methylmethacrylate-co-(fluoresceinO-acrylate)]; poly[methylmethacrylate-co-(fluoresceinO-methacrylate)]; poly{[2-[2',5'-bis(2"-ethylhexyloxy)phenyl]-1,4-phenylenevinylene]-co-[2-methoxy-5-(2'-ethylhexyloxy)-1,4-phenylenevinylene]}; poly[(methylmethacrylate)-co-(Disperse Red 1 acrylate)]; poly(4-hydroxy benzoic acid-co-ethylene terephthalate); poly(vinylidene chloride-co-acrylonitrile); poly(dimethylsiloxane-co-diphenylsiloxane), dihydroxy terminated; poly(1,4-butylene adipate-co-1,4-butylene succinate), extended with 1,6-diisocyanatohexane; poly(dicyclopentadiene-co-p-cresol); poly[ethyl acrylate-co-methacrylic acid-co-3-(1-isocyanato-1-methylethyl)-α-methylstyrene], adduct with ethoxylated nonylphenol solution; poly(epichlorohydrin-co-ethylene oxide); poly(Bisphenol A-co-4-nitrophthalic anhydride-co-1,3-phenylenediamine); poly(ethylene-co-methyl acrylate-co-acrylic acid); poly(propylene-co-1-butene); Nylon 6/66; poly(ethylene-co-acrylic acid) sodium salt; poly(ethylene-co-vinyl acetate-co-carbon monoxide); poly(melamine-co-formaldehyde), methylated/butylated (55/45); poly(maleic acid-co-olefin) sodium salt solution; poly(tetrafluoroethylene oxide-co-difluoromethylene oxide) α,ω-diisocyanate; poly(lauryl methacrylate-co-ethylene glycol dimethacrylate); poly[(phenyl isocyanate)-co-formaldehyde]; poly[2,6-bis(hydroxymethyl)-4-methylphenol-co-4-hydroxybenzoic acid]; poly(tetrafluoroethylene oxide-co-difluoromethylene oxide) α,ω-dicarboxylic acid; poly[methylmethacrylate-co-(Disperse yellow 7 acrylate)]; poly[(methylmethacrylate)-co-(9H-carbazole-9-ethylacrylate)]; poly[methylmethacrylate-co-(N-(1-naphthyl)-N-phenyl-methacrylamide)]; poly[(methylmethacrylate)-co-(Disperse Red 1 methacrylate)]; poly(L-lactide-co-caprolactone-co-glycolide); poly[methylmethacrylate-co-(7-(4-trifluoromethyl)coumarin acrylamide)]; poly[dimethylsiloxane-co-methyl(3,3,3-trifluoropropyl)siloxane]; poly[dimethylsiloxane-co-methyl(stearoyloxyalkyl)siloxane]; poly(hexafluoropropylene oxide-co-difluoromethylene oxide) alcohol, ethoxylated phosphate; poly(ethylene-co-1,2-butylene) mono-ol; poly[dimethylsiloxane-co-methyl(3-hydroxypropyl)siloxane]-graft-tetrakis(1,2-butylene glycol); poly(1,4-butylene adipate-co-polycaprolactam); poly(vinyl acetate-co-crotonic acid); poly(tert-butyl acrylate-co-ethyl acrylate-co-methacrylic acid); poly(1-vinylpyrrolidone-co-styrene); poly(tetrafluoroethylene oxide-co-difluoromethylene oxide)-α,ω-bis(methyl carboxylate); poly(vinylidene chloride-co-methyl acrylate); poly(acrylonitrile-co-vinylidene chloride-co-methyl methacrylate); poly(styrene-co-maleic anhydride), partial cyclohexyl/isopropyl ester, cumene terminated; poly(4-ethylstyrene-co-divinylbenzene); poly(dimethylsiloxane-co-dimer acid), bis(perfluorododecyl) terminated; poly(styrene-co-maleic anhydride), partial propyl ester, cumene terminated; poly(dimer acid-co-ethylene glycol), hydrogenated; poly(ethylene-co-glycidyl methacrylate); poly[dimethylsiloxane-co-methyl(3-hydroxypropyl)siloxane]-graft-poly(ethylene glycol) 3-aminopropyl ether; poly(dimer acid-co-1,6-hexanediol-co-adipic acid), hydrogenated; poly(3,3',4,4'-biphenyltetracarboxylic dianhydride-co-1,4-phenylenediamine), and amic acid solution; and poly[N,N'-bis(2,2,6,6-tetramethyl-4-piperidinyl)-1,6-hexanediamine-co-2,4-dichloro-6-morpholino-1,3,5-triazine].

In particular, the block copolymer can include an ABC triblock structure having a poly-butylacrylate segment, a poly-ethylacrylate segment, and a poly-methacrylic acid segment, for example. The block copolymer can include a diblock and/or triblock copolymer having two or more different poly-aliphatic-acrylate segments. In addition, the block copolymer can include a diblock and/or triblock copolymer having two or more poly-alkyl-acrylate segments.

In addition, the block copolymer can be used with, or in some embodiments replaced with, a detergent and/or a lipid. For example, the detergents can include, but are not limited to, AOT, brij family, Igepal family, triton family, SDS, and derivatives of each. In particular, the detergents can include, dioctyl sulfosuccinate sodium salt, polyethylene glycol dodecyl ether, octylphenoxy polyethoxyethanol, octylphenyl-polyethylene glycol, t-octylphenoxypolyethoxyethanol, polyethylene glycol tert-octylphenyl ether, 4-(1,1,3,3-tetramethylbutyl)phenyl-polyethylene glycol, dodecyl sulfate sodium salt, and glycolic acid ethoxylate octyl ether. Further, the block copolymer can include lipids such as, but not limited to, lipid-PEG, natural lipids, synthetic lipids, sphingolipids, and derivatives of each.

The nanostructure can be attached to a probe molecule. The probe molecule can be any molecule capable of being linked to the nanostructure either directly or indirectly via a linker. The probe molecule can be attached by any stable physical or chemical association to the nanostructure directly or indirectly by any suitable means.

In one embodiment, the probe molecule has an affinity for one or more target molecules (e.g., cancer cell) for which detection (e.g., determining the presence of and/or proximal position within the vessel (body)) is desired. If, for example, the target molecule is a nucleic acid sequence, the probe molecule should be chosen so as to be substantially complementary to the target molecule sequence, such that the hybridization of the target and the probe occurs. The term "substantially complementary," means that the probe molecules are sufficiently complementary to the target sequences to hybridize under the selected reaction conditions.

The probe molecule and the target molecule can include, but are not limited to, polypeptides (e.g., protein such as, but not limited to an antibody (monoclonal or polyclonal)), nucleic acids (both monomeric and oligomeric), polysaccharides, sugars, fatty acids, steroids, purines, pyrimidines, drugs (e.g., small compound drugs), ligands, or combinations thereof.

Use of the phrase "polypeptide" or "protein" is intended to encompass a protein, a glycoprotein, a polypeptide, a peptide, and the like, whether isolated from nature, of viral, bacterial, plant, or animal (e.g., mammalian, such as human) origin, or synthetic, and fragments thereof. A preferred protein or fragment thereof includes, but is not limited to, an antigen, an epitope of an antigen, an antibody, or an antigenically reactive fragment of an antibody.

Use of the phrase "nucleic acid" is intended to encompass DNA and RNA, whether isolated from nature, of viral, bacterial, plant or animal (e.g., mammalian, such as a human) origin, synthetic, single-stranded, double-stranded, comprising naturally or non-naturally occurring nucleotides, or chemically modified.

In addition, the probe can also include, but is not limited to, a drug, a therapeutic agent, radiological agent, a small molecule drug, and combinations thereof, that can be used to treat the target molecule and/or the associated disease and condition of interest. The drug, therapeutic agent, and radiological agent can be selected based on the intended treatment as well as the condition and/or disease to be treated. In an embodiment, the nanostructure can include two or more probes used to treat a condition and/or disease.

The following is a nonlimiting illustrative list of probes that can be used: PROLEUKIN™, CAMPATH™, PANRETIN™, ZYLOPRIM™, HEXALEN™, ETHYOL™, ARIMIDEX™, TRISENOX™, ELSPAR™, TICE BCG™, TARGRETIN™, BLENOXANE™, BUSULFEX™, MYLERAN™, METHOSARB™, XELODA™, PARAPLATIN™, BCNU™, BICNU™, GLIADEL WAFER™, CELEBREX™, LEUKERAN™, PLATINOL™, LEUSTATIN,-2-CDA™, CYTOXAN, NEOSAR™, CYTOXAN INJECTION™, CYTOXAN TABLET™, CYTOSAR-U™, DEPOCYT™, DTIC-DOME™, COSMEGEN™, ARANESP™, DANUOXOME™, DAUNORUBICIN™, CERUBIDINE™, ONTAK™, ZINECARD™, TAXOTERE™, ADRIAMYCIN, RUBEX™, ADRIAMYCIN PFS INJECTIONINTRAVENOUS INJECTION™, DOXIL™, DROMOSTANOLONE™, MASTERONE™, ELLIOTT'S B SOLUTION™, ELLENCE™, EPOGEN™, EMCYT™, ETOPOPHOS™, VEPESID™, AROMASIN™, NEUPOGEN™, FUDR™, FLUDARA™, ADRUCIL™, FASLODEX™, GEMZAR™, MYLOTARG™, ZOLADEX IMPLANT™, ZOLADREX™, HYDREA™, ZEVALIN™, IDAMYCIN™, IFEX™, GLEEVEC™, ROFERON-A™, INTRON A™, CAMPTOSAR™, FEMARA™, WELLCOVORIN, LEUCOVORIN™, LEUCOVORIN™, ERGAMISOL™, CEEBU™, MUSTARGEN™, MEGACE™, ALKERAN™, PURINETHOL™, MESNEX™, METHOTREXATE™, UVADEX™, MUTAMYCIN™, MITOZYTREX™, LYSODREN™, NOVATRONE™, DURABOLIN-50™, VERLUMA™, NEUMEGA™, ELOXATIN™, PAXENE™, TAXOL™, AREDIA™, ADAGEN (PEGADEMASE BOVINE)™, ONCASPAR™, NEULASTA™, NIPENT™, VERCYTE™, MITHRACIN™, PHOTOFRIN™, MATULANE™, ATABRINE™, ELITEK™, RITUXAN™, PROKINE™, ZANOSAR™, SCLEROSOL™, NOLVADEX™, TEMODAR™, VUMON™, TESLAC™, THIOGUANINE™, THIOPLEX™, HYCAMTIN™, FARESTON™, BEXXAR™, HERCEPTIN™, VESANOID™, URACIL MUSTARD CAPSULES™, VALSTAR™, VELBAN™, ONCOVIN™, NAVELBINE™, and ZOMETAT™.

In an embodiment, the nanostructure can include at least two different types of probes, one being a targeting probe that targets certain cells or compounds associated with a condition and/or disease, while the second probe is a drug used to treat the disease. In this manner, the nanostructure acts as a detection component, a delivery component to the cells of interest, and a delivery component for the treatment agent. The detection of the nanospecies can be used to ensure the delivery of the nanostructure to its intended destination as well as the quantity of nanostructures delivered to the destination.

The present disclosure provides methods of fabricating the nanostructures. See, Current Opinion in Biotechnology 2002, 13, 40-46; Nature Biotechnology 2004, 22, 969-976 both of which are incorporated herein by reference. An exemplary method is described in Example 1 below.

The present disclosure provides methods of detecting one or more target molecules in a sample or a subject (e.g., mammal, human, cat, dog, horse, etc.), and in particular, detect the target molecule in vivo. For example, the nanostructure can be used to detect the presence of a tumor in an animal using the nanostructures, as described in more detail in Example 1.

It should be noted that the nanospecies and block copolymers can self assemble into two dimensional or three dimensional microstructures via interactions such as, but not limited to, hydrophobic interactions, hydrophilic interactions, charge-charge interactions, π-stacking interactions, and combinations thereof. The self-assembly can be performed in a solution or emulsion, or on a substrate. The microstructure can be an ordered structure or a random structure. The microstructure can be composed of at least one nanoparticle and one block copolymer, or composed of multiple nanospecies and multiple block copolymers.

It should also be noted that preformed microstructures could be doped with one or more types of nanostructures. In particular, preformed microstructures prepared with block-copolymers (e.g., porous microstructures of one of many shapes (e.g., spherical)) can be doped with nanostructures via interactions such as, but not limited to, hydrophobic interactions, hydrophilic interactions, charge-charge interactions, and combinations thereof, depending on the nanostructures surface coating and block copolymer chemical composition.

As mentioned above, it should also be noted that nanostructures could be used for the detection of, as part of treatment (e.g., drug delivery), as an indication of delivery to one or more targets (e.g., cancers), and combinations thereof, conditions and/or diseases such as, but not limited to, cancers, tumors, neoplastic diseases, autoimmune diseases, inflammatory diseases, metabolic conditions, neurological and neurodegenerative diseases, viral diseases, dermatological diseases, cardiovascular diseases, an infectious disease, and combinations thereof.

In one embodiment, a single nanospecies coated with block copolymers, or nanoparticle-polymer composites containing one or more nanospecies, can be injected into subjects (e.g., humans, domesticated animals, and cattle) as a probe or contrast reagent for detection of primary tumors. These nanostructures can be linked to a bio-compatible compounds (e.g., PEG and dextran) for long-circulating "passive targeting" reagents, and/or linked to bio-affinity probes (e.g., antibody, antigen, peptide, oligonucleotide, small molecule ligand, and drugs) for "active" targeting of primary tumor.

It should be noted that a cell can be pre-labeled (e.g., in vitro and in vivo) with nanostructures and/or microstructures. For example, cells can be labeled with nanospecies-block copolymer microstructures in vitro through immuno staining, adsorption, microinjection, cell uptake, and the like. The cells then can be monitored in vitro, or traced in vivo with the nanoparticles as a tracer, fluorescence, magnetic, combinations thereof, and the like.

It should also be noted that nanostructures and/or microstructures can be used as an in vivo contrast reagent in the blood pool, the liver, the spleen, the heart, the lung, and the like. For example, nanoparticle-block copolymer microstructures can be injected into animals and by varying their structural properties, such as size and/or surface coating, these microstructures can preferentially localize into a particular organ or stay in the blood stream as a contrast reagent.

It should also be noted that block copolymers could be used to control the degradation of nanospecies. For example, block copolymers can be used to either protect (make bio-compatible) the nanospecies against degradation in biological conditions, especially for in vivo applications, or control the degradation rate/degree of the nanostructure, by varying the molecular structure of the block copolymer.

Cancer, as used herein, shall be given its ordinary meaning, is a general term for diseases in which abnormal cells divide without control. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth) and continue their rapid growth and division in this new location. This is called metastasis. Once malignant cells have metastasized, achieving cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

Cardiovascular disease, as used herein, shall be given its ordinary meaning, and includes, but is not limited to, high blood pressure, diabetes, coronary artery disease, valvular heart disease, congenital heart disease, arrthymia, cardiomyopathy, CHF, atherosclerosis, inflamed or unstable plaque associated conditions, restinosis, infarction, thromboses, post-operative coagulative disorders, and stroke.

Inflammatory disease, as used herein, shall be given its ordinary meaning, and can include, but is not limited to, autoimmune diseases such as arthritis, rheumatoid arthritis, multiple sclerosis, systemic lupus erythematosus, other diseases such as asthma, psoriasis, inflammatory bowel syndrome, neurological degenerative diseases such as Alzheimer's disease, Parkinson's disease, Huntington's disease, vascular dementia, and other pathological conditions such as epilepsy, migraines, stroke and trauma.

Autoimmune disease, as used herein, shall be given its ordinary meaning, and includes, but is not limited to, alopecia areata, ankylosing spondylitis, antiphospholipid syndrome, autoimmune Addison's disease, aplastic anemia, autoimmune hemolytic anemia, autoimmune hepatitis, Behcet's disease, biliary cirrhosis, bullous pemphigoid, canavan disease, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dermatomyositis, diffuse cerebral sclerosis of Schilder, discoid lupus, essential mixed cryoglobulinemia, fibromyalgia-fibromyositis, Fuch's heterochromic iridocyclitis, Graves' disease, Guillain-Barr, Hashimoto's thyroiditis, idiopathic pulmonary fibrosis, idiopathic thrombocytopenia purpura (ITP), IgA nephropathy, insulin dependent diabetes, intermediate uveitis, juvenile arthritis, lichen planus, lupus, Mnire's disease, mixed connective tissue disease, multiple sclerosis, myasthenia gravis, nephrotic syndrome, pemphigus vulgaris, pernicious anemia, polyarteritis nodosa, polychondritis, polyglandular syndromes, polymyalgia rheumatica, polymyositis and dermatomyositis, primary Agammag-lobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, vasculitis, vitiligo, VKH (Vogt-Koyanagi-Harada) disease, Wegener's granulomatosis, anti-phospholipid antibody syndrome (lupus anticoagulant), Churg-Strauss (allergic granulomatosis), dermatomyositis/polymyositis, Goodpasture's syndrome, interstitial granulomatous dermatitis with arthritis, lupus erythematosus (SLE, DLE, SCLE), mixed connective tissue disease, relapsing polychondritis, HLA-B27 associated conditions including ankylosing spondylitis, psoriasis, ulcerative colitis, Reiter's syndrome, and Uveal diseases.

Viral disease, as used herein, shall be given its ordinary meaning, and includes target viruses such as, but not limited to, paramyxo-, picoma-, rhino-, coxsackie-, influenza-, herpes-, adeno-, parainfluenza-, respiratory syncytial-, echo-, corona-, Epstein-Barr-, cytomegalo-, varicella zoster, and hepatitis (e.g., variants including hepatitis C Virus (HCV), Hepatitis A Virus (HAV), Hepatitis B Virus (HBV), Hepatitis D Virus (HDV), Hepatitis E Virus (HEV), Hepatitis F Virus (HFV), Hepatitis G Virus (HGV), Human immunodeficiency).

Neurological conditions, as used herein, shall be given its ordinary meaning, can be generally classified into three classes: those disease with ischemic or hypoxic mechanisms; neurodegenerative diseases (see Adams et al, Principles of Neurology, 1997, $6^{th}$ Ed., New York, pp 1048); and neurological and psychiatric diseases associated with neural cell death.

Diseases with ischemic or hypoxic mechanisms can be further subclassified into general diseases and cerebral ischemia. Examples of such general diseases involving ischemic or hypoxic mechanisms include myocardial infarction, cardiac insufficiency, cardiac failure, congestive heart failure, myocarditis, pericarditis, perimyocarditis, coronary heart disease (stenosis of coronary arteries), angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, and pulmonary edema. Examples of cerebral ischemia disease include stroke (as well as hemorrhagic stroke), cerebral microangiopathy (small vessel disease), intrapartal cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, and diabetic retinopathy.

Neurodegenerative disease can include, but is not limited to, amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Straussler-Schanke-r disease, Creutzfeld-Jakob-disease, Machado-Joseph disease, Friedreich ataxia, Non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome.

Examples of neurological and psychiatric diseases associated with neural cell death include septic shock, intracerebral bleeding, subarachnoidal hemorrhage, multiinfarct dementia, inflammatory diseases (e.g., vasculitis, multiple sclerosis, and Guillain-Barre-syndrome), neurotrauma (e.g., spinal cord trauma, and brain trauma), peripheral neuropathies, polyneuropathies, epilepsies, schizophrenia, metabolic encephalopathies, and infections of the central nervous system (e.g., viral, bacterial, fungal).

EXAMPLE 1

Now having described the embodiments of the nanostructure in general, example 1 describes some embodiments of the nanostructure and uses thereof. The following is a non-limiting illustrative example of an embodiment of the present invention that is described in more detail in Gao et al, Nature Biotechnology, 22, 8 (2004), which is incorporated herein by reference. This example is not intended to limit the scope of any embodiment of the present disclosure, but rather is intended to provide specific experimental conditions and results. Therefore, one skilled in the art would understand that many experimental conditions can be modified, but it is intended that these modifications be within the scope of the embodiments of the present disclosure.

Multifunctional nanoparticle probes based on semiconductor quantum dots (QDs) have been developed for cancer targeting and imaging in living animals. The structural design involves encapsulating luminescent QDs with an ABC triblock copolymer, and linking this amphiphilic polymer to tumor-targeting ligands and drug-delivery functionalities. In vivo targeting studies of human prostate cancer growing in nude mice indicate that the QD probes can be delivered to tumor sites by both enhanced permeation and retention and by antibody binding to cancer-specific cell surface biomarkers. The use of both subcutaneous injection of QD-tagged cancer cells and systemic injection of multifunctional QD probes resulted in the sensitive and multicolor fluorescence imaging of cancer cells under in vivo conditions. This example also reports the integration of a whole-body macro-illumination system with wavelength-resolved spectral imaging for efficient background removal and precise delineation of weak spectral signatures. These results raise new possibilities for ultrasensitive and multiplexed imaging of molecular targets in vivo.

Results

Figure 3A:
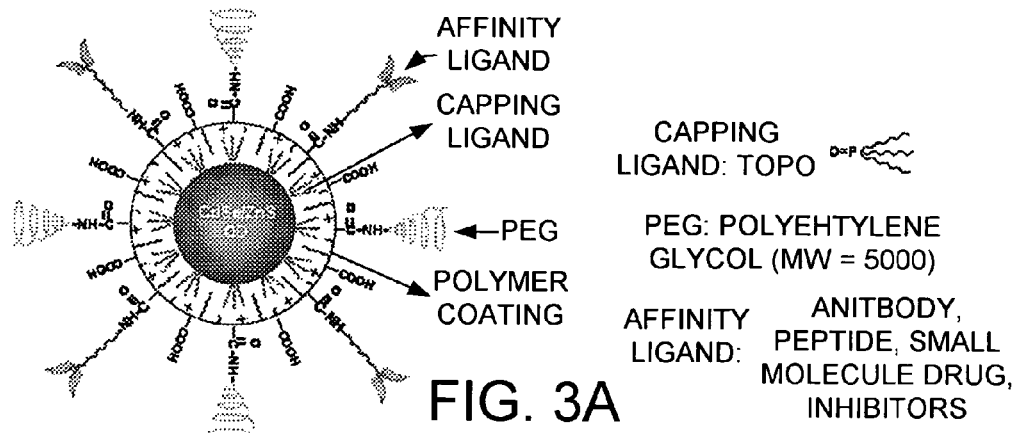
FIG. 3A illustrates a schematic of bioconjugated quantum dots for in vivo cancer targeting and imaging.
Figure 3B:
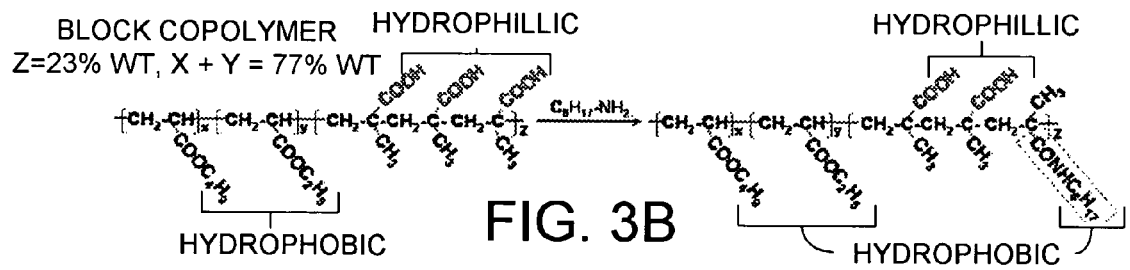
FIG. 3B illustrates a chemical modification of a triblock copolymer with an 8-carbon side chain.

Probe Design: Bioconjugated QD probes for in vivo cancer targeting and imaging were designed by using drug delivery and targeting principles. As schematically illustrated in (FIG. 3A), core-shell CdSe—ZnS quantum dots are protected by both a coordinating ligand (TOPO) and an amphiphilic polymer coating. Due to strong hydrophobic interactions between TOPO and the polymer hydrocarbon, these two layers "bond" to each other and form a hydrophobic protection structure that is resistant against hydrolysis and enzymatic degradation even under complex in vivo conditions. In contrast to simple polymers and amphiphilic lipids used in previous studies, the methods described herein use a high-molecular-weight (MW=about 100 kD) copolymer with an elaborate ABC triblock structure and a grafted 8-carbon (C-8) alkyl side chain (FIG. 3B). This triblock polymer includes a polybutylacrylate segment (hydrophobic), a polyethylacrylate segment (hydrophobic), a polymethacrylic acid segment (hydrophilic), and a hydrophobic hydrocarbon side chain. A key finding is that this polymer can disperse and encapsulate single TOPO-capped QDs via a spontaneous self-assembly process. As a result, the QDs are protected to such a degree that their optical properties (e.g., absorption spectra, emission spectra, and fluorescence quantum yields) did not change in a broad range of pH (1 to 14) and salt conditions (0.01 to 1 M) or after harsh treatment with 1.0 M hydrochloric acid (PEG-linked QDs).

Dynamic light scattering (DLS) measurement indicates that the assembled QD probes have a hydrodynamic radius of about 10 through 15 nm (depending on attached ligands). This value agrees with a compact probe structure consisting of a 5-nm QD core (2.5 nm radius), a 1-nm TOPO cap, a 2-nm thick polymer layer, and a 4-5-nm PEG/antibody layer. It has been suggested that the hydrodynamic radii of QDs could be considerably larger than their TEM "dry" radii, but the reported TEM values do not represent the true physical sizes of organic-coated QDs. The reason is that organic materials (such as TOPO, polymers, and conjugated biomolecules) are not electron-dense enough for TEM visualization on the nanometer scale. Since QDs are tightly protected from contacting the outside environment, their hydrodynamic behavior is mainly controlled by the surface-coating layer. As such, the polymer-coated quantum dots should behave similarly as standard polymer micelles or nanoparticles, and there is no fundamental reason for coated QDs to have unusual hydrodynamic properties in comparison with macromolecules and nanoparticles.

Based on the geometric/size constraints and the ligand coupling efficiencies (about 40-50%, experimentally determined by using fluorescently labeled ligands), it has been estimated that each dot contains about 200 TOPO molecules, about 4 to 5 triblock copolymer molecules, about 5 to 6 PEG molecules, and about 5 to 6 antibody molecules. High-sensitivity fluorescence imaging showed "blinking" signals when a dilute solution ($10^{-12}$ M) of the QD bioconjugate was spread on a glass surface. This blinking behavior is characteristic of single quantum systems such as single dye molecules and single QDs, indicating that the triblock copolymer has efficiently dispersed the dots into single particles. Preliminary TEM results also revealed that the QD probes consisted of single particles, with little or no aggregation. It is worth noting, however, that QD blinking has no adverse implications for in vivo tumor imaging because the tumor cells are labeled with a large population (up to millions) of QDs, far from the single-dot regime.

At the current level of PEG conjugation, it does not interfere with antibody binding, as confirmed by positive cellular staining. At higher PEG densities or longer chains, significant interference with ligand binding could occur, as reported previously for pegylated liposomes. To reduce interference, the targeting ligands could be attached to the distal termini of PEG. The fully exposed ligands, however, could elicit non-specific cellular uptake or an immune response, thus reducing the probe's biocompatibility and duration of circulation in vivo.

Figure 3C:
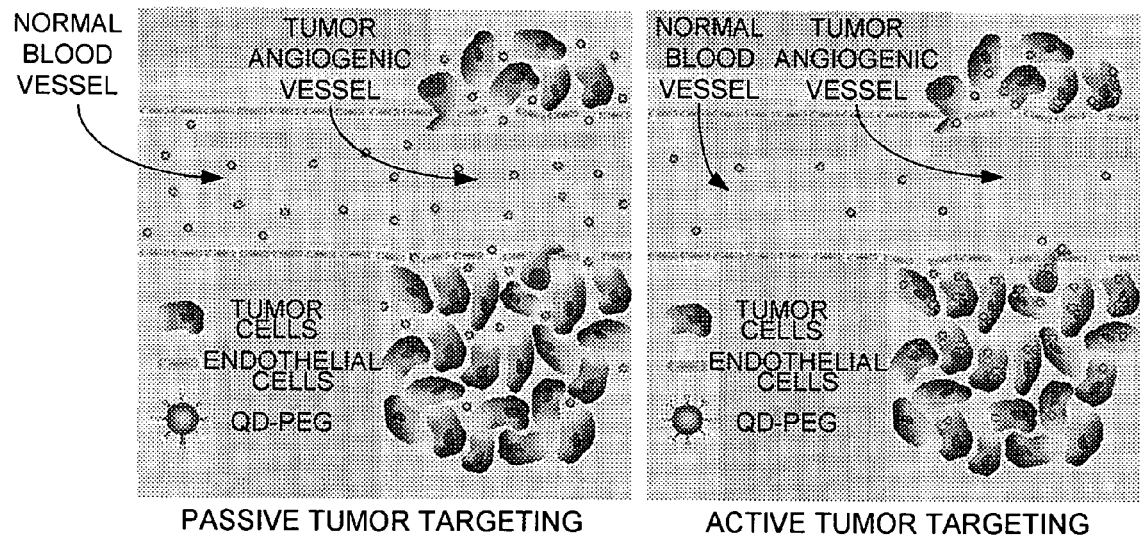
FIG. 3C illustrates the permeation and retention of QD probes via leaky tumor vasculatures (passive targeting), and high affinity binding of QD-antibody conjugates to tumor antigens (active targeting).

Tumor Targeting: Under in vivo conditions, QD probes can be delivered to tumors by both a passive targeting mechanism and an active targeting mechanism (FIG. 3C). In the passive mode, macromolecules and nanometer-sized particles are accumulated preferentially at tumor sites through an enhanced permeability and retention (EPR) effect. This effect is believed to arise from two factors: (a) angiogenic tumors that produce vascular endothelial growth factors (VEGF) that hyperpermeabilize the tumor-associated neovasculatures and cause the leakage of circulating macromolecules and small particles; and (b) tumors lack an effective lymphatic drainage system, which leads to subsequent macromolecule or nanoparticle accumulation. For active tumor targeting, antibody-conjugated quantum dots have been used to target a prostate-specific cell surface antigen, PSMA. Previous research has identified PSMA as a cell surface marker for both prostate epithelial cells and neovascular endothelial cells. PSMA has been selected as an attractive target for both imaging and therapeutic intervention of prostate cancer. Accumulation and retention of PSMA antibody at the site of tumor growth is the basis of radioimmunoscintigraphic scanning (e.g., ProstaScint scan) and targeted therapy for human prostate cancer metastasis.

Figure 4:
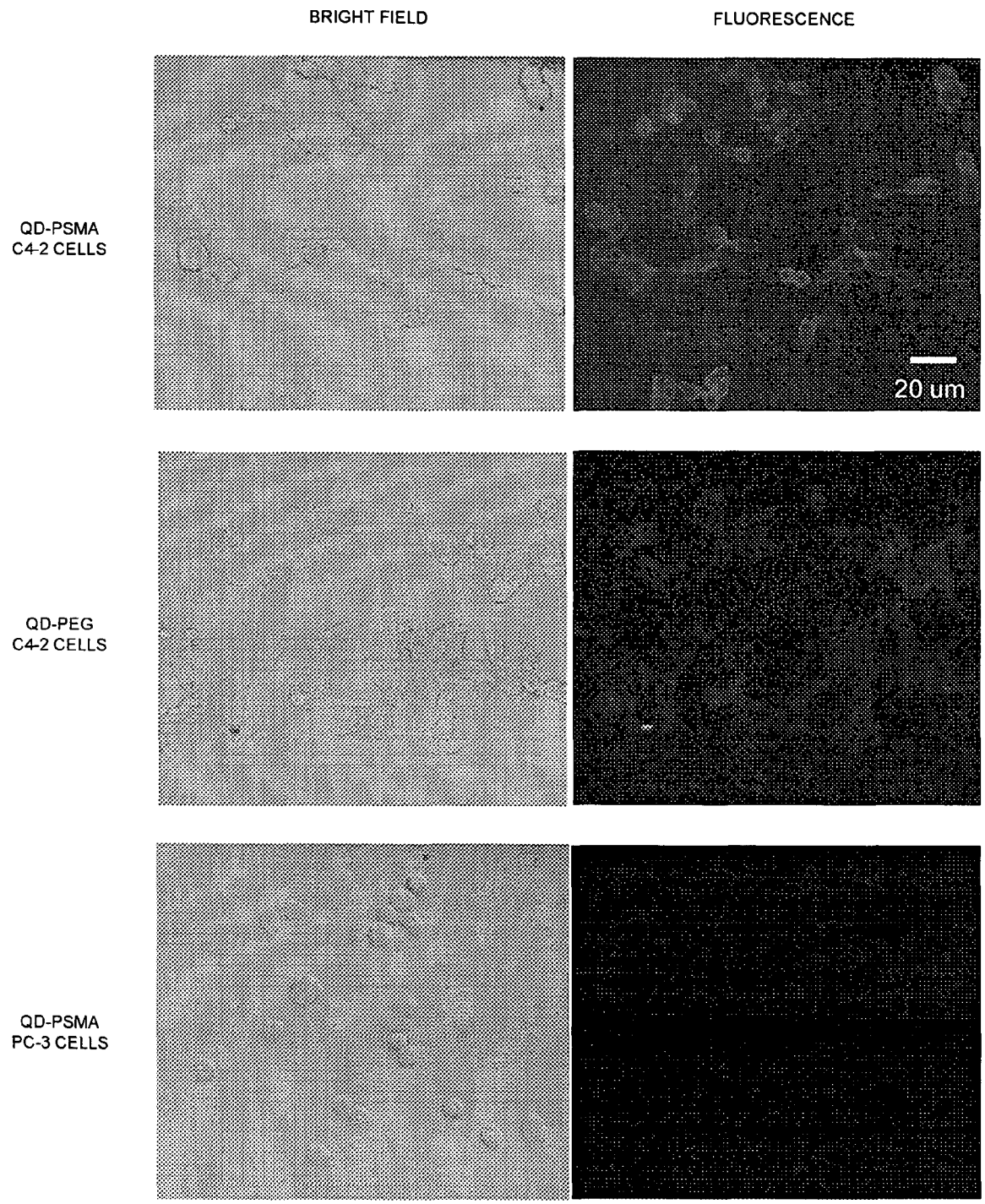
FIG. 4 illustrates immunocytochemical studies of QD-PSMA antibody (Ab) binding activity in cultured prostate cancer cells. The top panels illustrate bright-field and fluorescence images that were obtained for PSMA-positive C4-2 cells as revealed by the presence of QD-PSMA-Ab complex on the cell surface. The middle panels illustrate negative staining that was detected in C4-2 cells exposed to QD-PEG in the absence of PSMA Ab. The bottom panels illustrate negative staining that was noted in PC-3 cells, which lack PSMA expression.

The QD probes conjugated to a PSMA monoclonal antibody, J591, which recognizes the extracellular domain of PSMA, were first evaluated for binding to PSMA in prostate cancer cell lines. Immunocytochemical data confirmed strong and specific binding of the PSMA Ab J591-conjugated QD probes to a human prostate cancer cell line, C4-2, which is known to express PSMA on the cell surface (FIG. 4, top panels). Control studies using QD-PEG (without antibody) showed only a low level of nonspecific cell binding to C4-2 cells (FIG. 4, middle panels). Additional control studies using PC-3 cells, a PSMA negative human prostate cancer cell line, also showed the absence of QD binding (FIG. 4, lower panels). These results establish that the PSMA antibody-QD conjugates retain their PSMA binding activity and specificity.

Figure 5A:
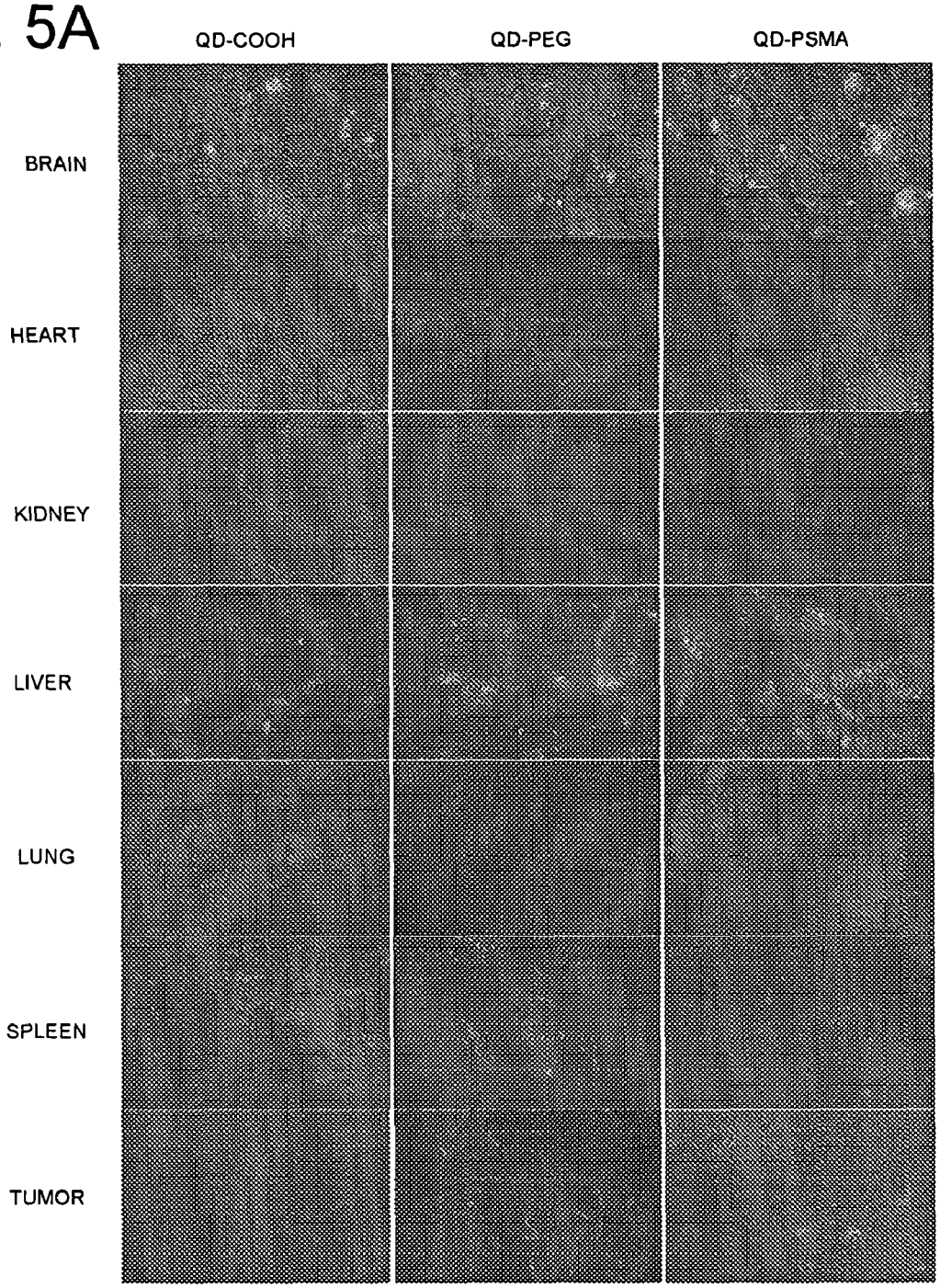
FIGS. 5A and 5B illustrate a histological examination of QD uptake, retention, and distribution in six different normal host organs (FIG. 5A) and in C4-2 tumor (FIG. 5B) xenografts maintained in athymic nude mice. QD uptake and retention was evaluated by using three surface modifications as indicated by the left, middle, and right columns. In the left column the QD is coated with surface carboxylic acid groups (6.0 nmol and 6 hrs circulation). In the middle column the QD is surface coated with PEG groups (6.0 nmol and 24 hrs circulation). In the right column the QD is surface modified by PEG and bioconjugated with a PSMA antibody (0.4 nmol and 2 hrs circulation). The left and middle columns are the same except that the amount of QD injection was all reduced to 0.4 nmol and the circulation was reduced to 2 hours. All images were obtained from 5-10 µm-thin tissue sections on an epi-fluorescence microscope. All the tumors had similar sizes, measuring about 0.5-1 cm in diameter along the long axis. QDs were detected by their characteristic red-orange fluorescence, and all other signals were due to background autofluorescence.
Figure 5B:
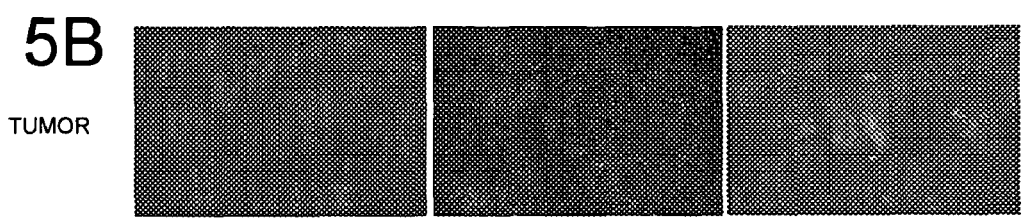

To investigate the behavior of QD-PSMA Ab conjugated probes in living animals, the following were examined in the present study: their specific uptake and retention, background or nonspecific uptake, blood clearance, and organ distribution as well as their relationship to QD surface modifications. FIGS. 5A and 5B show comparative histological data of a tumor xenograft (FIG. 5B) and six normal host organs (FIG. 5A) obtained from a nude mouse after a single tail vein administration of QD-PSMA Ab conjugate. As seen from the characteristic red-orange fluorescence of quantum dots, nonspecific QD uptake and retention took place primarily in the liver and the spleen, with little or no QD accumulation in the brain, the heart, the kidney, or the lung. This pattern of in vivo organ uptake and distribution is similar to that of dextran-coated magnetic iron oxide nanoparticles. For polymer-encapsulated QDs with excess COOH groups, no tumor targeting was observed, indicating nonspecific organ uptake and rapid blood clearance. For polymer-encapsulated QDs with surface PEG groups, the rate of organ uptake was reduced and the length of blood circulation was improved, leading to slow accumulation of the nanoparticles in the tumors. For QDs encapsulated by PEG and bioconjugated with PSMA antibody, the nanoparticles were delivered and retained by the tumor xenografts, but nonspecific liver and spleen uptake was still apparent.

Passive tumor targeting was observed only with an increased dose of QD-PEG conjugate (6 nmol injected plus a 24-hour latent period of probe circulation). In contrast, this same dose of QD-COOH conjugate was found to have little accumulation in tumors due to passive targeting following the same length of circulation in athymic hosts. This low efficiency of QD uptake and retention is likely due to the excess negative charges on the probe surface (free carboxylic acid groups on the polymer coating), which is known to reduce the rate of probe extravasation and its subsequent accumulation into tumor xenografts.

Figure 6A:
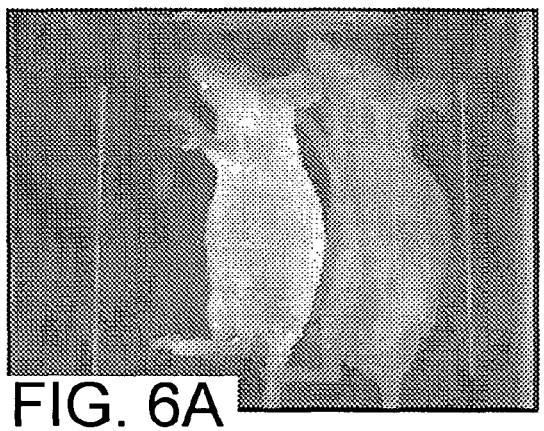
FIGS. 6A through 6D illustrate spectral imaging of QD-PSMA Ab conjugates in live animals harbored with C4-2 tumor xenografts. Orange-red fluorescence signals indicate a prostate tumor growing in a live mouse (FIGS. 6B and 6D). Control studies using a healthy mouse (no tumor) and the same amount of QD injection showed no localized fluorescence signals (FIGS. 6A and 6C).
Figure 6B:
Figure 6C:
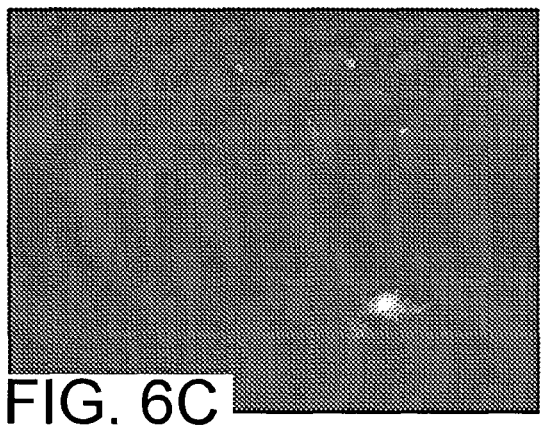
Figure 6D:

In vivo Cancer Imaging: FIGS. 6A through 6D depict spectral imaging results obtained from PSMA-Ab QD probes injected into the tail vein of a tumor-bearing mouse and a control mouse (no tumor). The original image (FIG. 6A) shows QD signals at one tumor site among an autofluorescence background (mouse skin). Using spectral unmixing algorithms, the fluorescence background signals (FIG. 6B) can be separated from the QD signals. (FIG. 6C). The composite image (FIG. 6D) clearly shows the whole animal and the tumor site. The enhanced contrast in the bottom right image indicates that the QD probes can be visualized against an essentially black background, with little or no interference from the mouse autofluorescence. Results from separate tests using quantum dots excited in vitro indicate that spectral imaging techniques can be used to unmix multiple fluorescent signals that differ by as little as 5 nm in peak position (results not shown). Thus, the ability to exclude interference from autofluorescence and the capability of resolving multiple simultaneous labels suggest that spectral imaging will have considerable utility when combined with quantum-dot-based labeling strategies.

Figure 7:
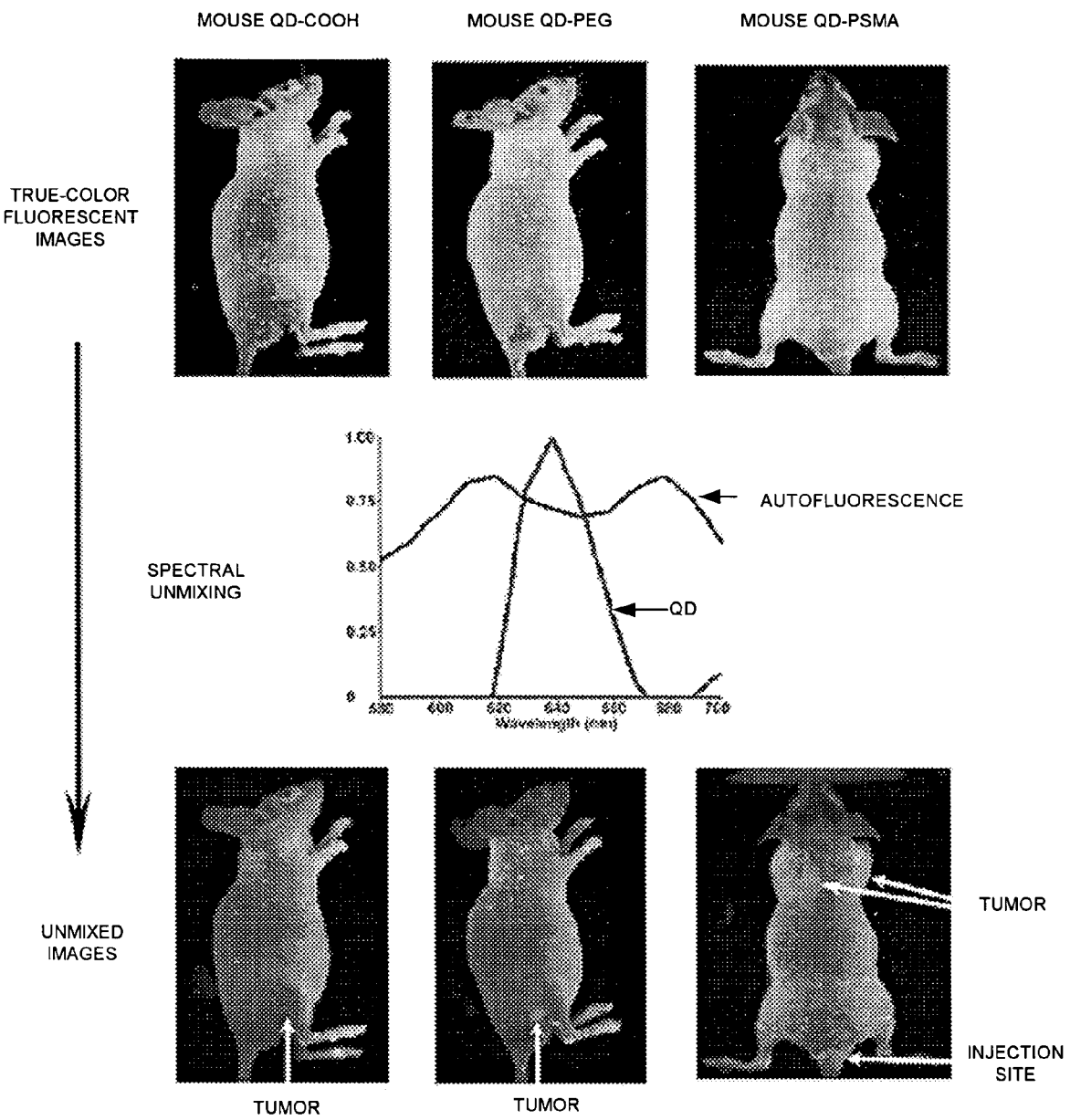
FIG. 7 illustrates in vivo fluorescence images of tumor-bearing mice using QD probes with three different surface modifications: carboxylic acid groups (left), PEG groups (middle), and PEG-PSMA Ab conjugates (right). For each surface modification, a color image (top), two fluorescence spectra from QD and animal skin (middle), and a spectrally resolved image (bottom) were obtained from the live mouse models bearing C4-2 human prostate tumors of similar sizes (0.5-1.0 cm in diameter). The amounts of injected QDs and the lengths of circulation were: 6 nmol and 6 hours for the COOH probe; 6 nmol and 24 hours for the PEG probe; and 0.4 nmol and 2 hours for the PSMA probe (same as in FIG. 4). The site of QD injection was observed as a red spot on the mouse tail. The spectral feature at about 700 nm (QD curve, middle panel) was an artifact caused by mathematical fitting of the original QD spectrum, which has little or no effect on background removal.

The present study has further examined how functional groups on the QD probe surface affect in vivo imaging results. FIG. 7 compares the in vivo imaging results from three types of surface modifications: COOH groups, PEG groups, and PEG plus PSMA Ab. In agreement with histological examinations, no tumor signals were detected with the COOH probe; only weak tumor signals were observed with the PEG probe (passive targeting); and intense signals were detected in the PEG-PSMA Ab conjugated probe (active targeting). This comparison provides further evidence that active tumor targeting by using a tumor-specific ligand is much faster and more efficient than passive targeting based on tumor permeation, uptake and retention.

Probe Brightness and Spectral Comparison with GFP: Since genetically encoded fluorescent proteins such as GFP have been used to tag cells for in vivo cancer imaging, it is important to compare the detection sensitivity and spectral features of GFP and QD probes. For this purpose, QDs were first linked to a translocation peptide (such as HIV Tat or polyarginine), and were delivered into living cancer cells. Similar peptides have been used to deliver magnetic nanoparticles into living cells for in vivo monitoring of cell migration and integration. Fluorescence intensity measurement indicates that as many as three million QDs can be delivered into each cancer cell. Surprisingly, this level of QD loading did not affect cell viability and growth, because the implantation of QD-tagged cancer cells led to usual tumor growth in animal models.

Figure 8A:
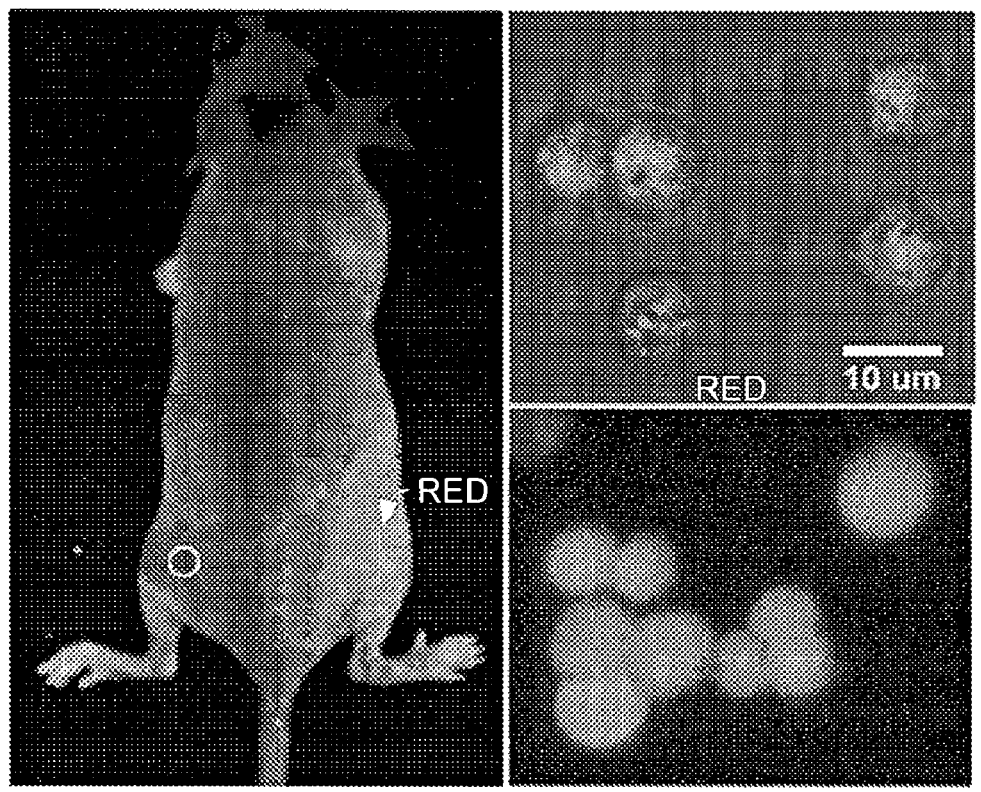
FIG. 8A illustrates a sensitivity and spectral comparison between QD-tagged and GFP-transfected cancer cells.

FIG. 8A shows in vivo imaging data for the same number (about 1000) of QD-tagged cells and GFP stably transfected cells that were injected into each side of a host mouse. Although the QD-tagged cells and the GFP transfected cells were similarly bright in cell cultures (two images on the right), only the QD signal was observed in vivo (orange glow on the right flank). No GFP signals could be discerned at the injection site (circle on the left flank). This result does not provide an absolute intensity comparison between GFP and QDs because several factors (such as optical density and tissue scattering) are difficult to normalize or calibrate. Instead, it is a qualitative spectral comparison demonstrating that the emission spectra of QDs can be shifted away from the autofluorescence, allowing spectroscopic detection at low signal intensities. In contrast, organic dyes and fluorescent proteins give rise to small Stokes shifts, resulting GFP emission and background fluorescence in the same spectral region. The brightness and spectral shifting advantages of QDs are further shown in FIGS. 9A and 9B and 10A and 10B.

Another important feature is the large absorption coefficients of QDs, which makes them brighter probes under photon-limited in vivo conditions (where light intensities are severely attenuated by scattering and absorption). To appreciate this feature, the photophysics of quantum dots and organic dyes can be compared. In theory, the lifetime-limited emission rates for single quantum dots are 5-10 times lower than those of single organic dyes because of their longer excited state lifetimes (20-50 ns). In practice, however, fluorescence imaging usually operates under absorption-limited conditions, in which the rate of absorption is the main limiting factor of fluorescence emission. Since the molar extinction coefficients ($0.5$-$2\times10^6$ $M^{-1}$ $cm^{-1}$) of QDs are about 10-50 times larger than that ($5$-$10 \times 10^4$ $M^{-1}$ $cm^{-1}$) of organic dyes, the QD absorption rates will be 10-50 times faster than that of organic dyes at the same excitation photon flux. Due to this increased rate of light emission, single QDs appear 10-20 times brighter than organic dyes, a result that has been experimentally confirmed by the current literature.

Figure 8B:
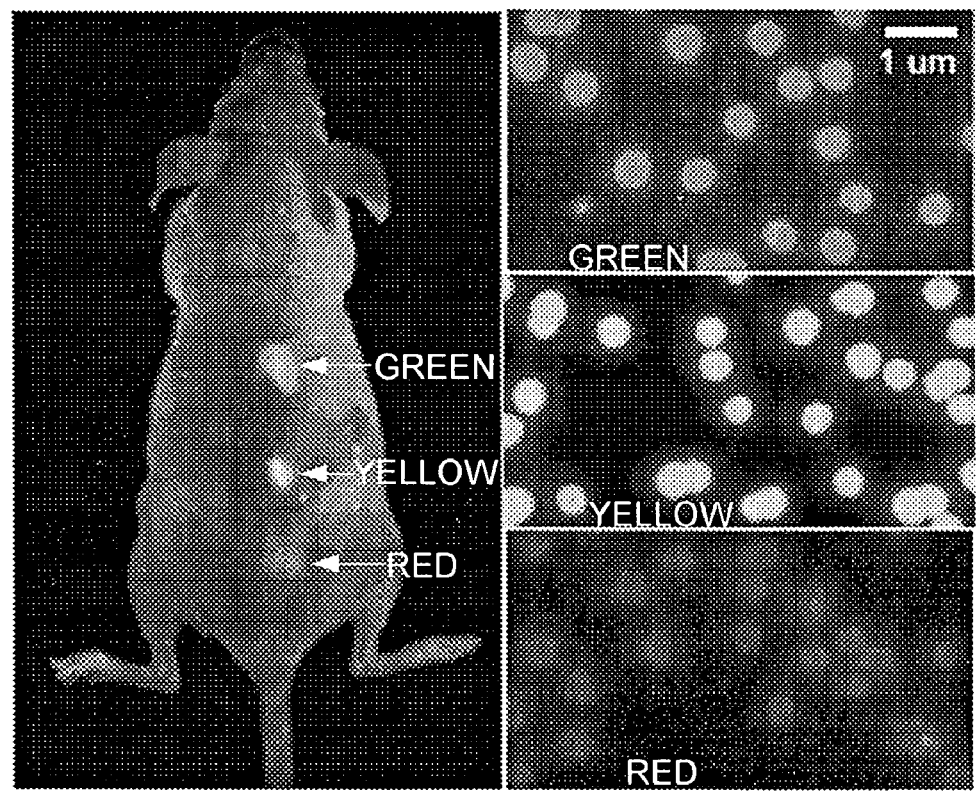
FIG. 8B illustrates a simultaneous in vivo imaging of multicolor QD-encoded microbeads. The right-hand images in FIGS. 8A and 8B show QD-tagged cancer cells (upper) and GFP-labeled cells (lower).
Figure 9A:
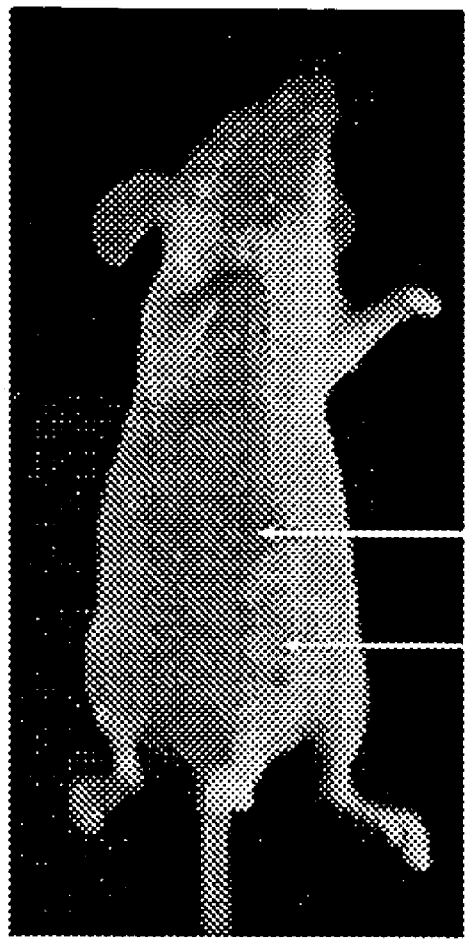
FIGS. 9A and 9B illustrate a comparison of red-emitting QDs and red organic dyes for in vivo optical imaging.
Figure 9B:
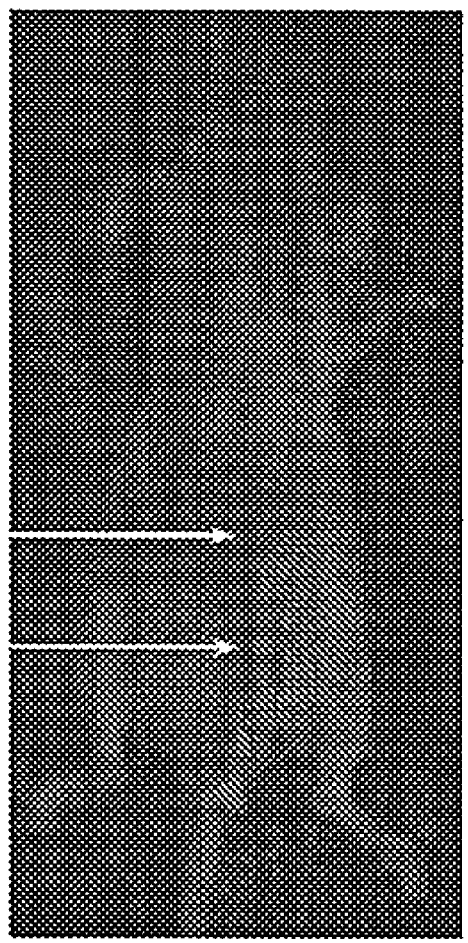

The present study has further explored multicolor in vivo imaging with QD-encoded microbeads. For this purpose, three samples of 0.5 μm polymer beads, each doped with green, yellow or red QDs, were injected into a mouse model at three different locations, similar to previous reports of using fluorescent beads for cell differentiation and trafficking studies. Due to the usually large Stokes shifts and broad excitation profiles of QDs, all three colors were observed simultaneously in the same mouse and with a single light source (FIG. 8B).

Discussion

Prior to this work, several groups have reported the use of QDs for sensitive bioassays and cellular imaging, but a significant loss of fluorescence has been noted upon the administration of quantum dots into live animals. While the exact origin of this signal loss is still not clear, recent research suggests that the surface ligands and coatings are slowly degraded in body fluids, leading to surface defects and fluorescence quenching. This mechanism is supported by the observation that the surface defects can be annealed by continuous laser excitation, and the loss of QD fluorescence can be partially restored (involving surface structural changes). The QD probes reported in this work represent a significant improvement because they are highly stable against in vivo degradation. An important feature is a high-molecular-weight triblock copolymer, which completely encapsulates TOPO-QDs and forms a stable hydrophobic protection layer around single QDs.

On the hydrophilic surface of this polymer layer, there is a large number of functional groups (e.g., about 400 to 500 carboxylic acids groups), which allows the attachment of both diagnostic and therapeutic agents. With small-molecule ligands such as synthetic organic molecules, short oligonucleotides and peptides, many copies of the same ligand can be linked to single dots, leading to multivalent QD-target binding. Previous research has shown that properly designed multivalent ligands can increase the binding affinity by 10 orders of magnitude. Using colloidal gold nanoparticles linked to oligos at high surface densities, it has been demonstrated that the sequence selectivity of DNA hybridization can be improved by 100 to 1000 times (sharper melting curves). Research has also shown that QD-peptide conjugates exhibit exquisite binding specificity, most likely due to multivalent peptide binding to protein targets distributed on the surface of tumor vasculature. This novel feature is not available with organic dyes and fluorescent proteins, and could allow the design of multivalent QD probes to target cancer cells based on the density and distribution of biomarkers on the cell surface. This might offer a new strategy for cancer molecular diagnosis and therapy because truly unique cancer biomarkers are often not available or are present at extremely low concentrations.

In addition, the polymer-encapsulated QD probes are in an excellent size range for in vivo tumor targeting. With small peptide-dye conjugates, rapid extravasation often leads to blood clearance of the probe in less than one minute. The circulation or retention time can be improved by attaching small probes to macromolecules or nanoparticles, a strategy widely used in drug delivery research. Indeed, the described work indicates that PEG-shielded QDs are able to circulate in blood for as long as about 48-72 hours, with a half decay time of about 5-8 hours. At the same time, these probes are small enough for efficient binding to cell surface receptors, for internalization through endocytosis or peptide translocation, and for passing through the nuclear pores to enter the cell nucleus (using nuclear-localization peptides) (FIG. 8A, top right). However, the penetration depth of QDs into solid tumors will be limited, at least in part, by their nanometer sizes.

The unique optical properties of QDs also provide new opportunities for multicolor imaging and multiplexing. For example, multicolor imaging will allow intensity ratioing, spatial colocalization, and quantitative target measurements at metastatic tumor sites. Optical encoding strategies are also possible based on the use of multiple colors and multiple intensity levels. This combinatorial approach has been demonstrated for tagging a large number of genes, proteins, and small-molecule libraries. In addition to wavelength and intensity, lifetime fluorescence imaging represents a new dimension. Because the excited state lifetimes (about 20-50 ns) of QDs are nearly one order magnitude longer than that of organic dyes (about 2-5 ns), QD probes should be suitable for fluorescence lifetime imaging (FLIM) of cells, tissue specimens, and living animals.

The current use of orange/red-emitting quantum dots is not optimized for tissue penetration or imaging sensitivity. Extensive work in tissue optics has shown deep tissue imaging (millimeters to centimeters) requires the use of far-red and near-infrared light in the spectral range of 650-900 nm. This wavelength range provides a "clear" window for in vivo optical imaging because it is separated from the major absorption peaks of blood and water. Based on tissue optical calculations, it is estimated that the use of near-infrared-emitting quantum dots should improve the tumor imaging sensitivity by at least 10-fold, allowing sensitive detection of 10-100 cancer cells. Toward this goal, recent research has prepared a new class of alloyed semiconductor quantum dots consisting of cadmium selenium telluride, with tunable fluorescence emission up to 850 nm and quantum yields up to 60%. Together with core-shell CdTeCdSe type-II materials, the use of near-infrared-emitting QDs should bring major improvements in tissue penetration depth and cell detection sensitivity.

A remaining issue is the QD's toxicity and metabolism in vivo. Recent work indicates that CdSe QDs are highly toxic to cells under UV illumination for extended periods of time. This is understandable because UV-irradiation often dissolves the semiconductor particles, releasing toxic cadmium ions into the medium. In the absence of UV irradiation, the present work shows that QDs with a stable polymer coating are essentially nontoxic to cells (no effect on cell division or ATP production). Current literature shows that in vivo studies also confirmed the nontoxic nature of stably protected QDs. This is perhaps not surprising because the polymer protection layer is so stable that the QD core would not be exposed to the outside environment. Consistent with this conclusion, previous research has shown that the uptake of dextran-protected iron oxide nanoparticles (up to 10 million particles per cell) does not significantly reduce cell viability, and that the injection of micelle-protected QDs (up to 2 billion per embryo cell) does not affect frog embryo development. In this work, up to 3 million QDs in a single cancer cell did not appreciably reduce its viability or growth.

At the present, however, little is known about the mechanism of metabolism or clearance of QD probes injected into living animals. For the polymer-encapsulated QDs, chemical or enzymatic degradations of the semiconductor cores are unlikely to occur. But the polymer-protected QDs might be cleared from the body by slow filtration and excretion through the kidney.

In conclusion, the present study involves the development of a new class of polymer-encapsulated and bioconjugated QD probes for cancer targeting and imaging in vivo. These probes are bright, stable, and have a versatile triblock copolymer structure that is well suited for conjugation to additional diagnostic and therapeutic agents. In vivo imaging results indicate the QD probes can be targeted to tumor sites through both passive and active mechanisms, but passive targeting is much slower and less efficient than active targeting. When combined with wavelength-resolved imaging, the QD probes allow sensitive and multicolor imaging of cancer cells in living animals. The use of near-infrared-emitting quantum dots should improve both the tissue penetration depth and imaging sensitivity. In accordance with the described study, quantum dots could be integrated with targeting, imaging, and therapeutic agents to develop "smart" nanostructures for noninvasive imaging, diagnosis, and treatment of cancer, cardiovascular plaques, and neurodegenerative disease.

Methods: Animal use protocols were reviewed and approved by the Institutional Animal Care and Use Committee of Emory University.

Materials: Except noted otherwise, all chemicals and biochemicals were purchased from Sigma-Aldrich (St. Louis, Mo.) and were used without further purification. A monoclonal antibody (J591) to prostate-specific membrane antigen (PSMA) was a kind gift from Millennium Pharmaceuticals (Cambridge, Mass.). Membrane translocation peptides (Tat and polyarginine, with a c-terminal biotin for conjugation to strepavidin-QD) was synthesized and purified by Invitrogen (Carlsbad, Calif.). Core-shell quantum dots (ZnS-capped CdSe) were synthesized according to literature procedures. A high-temperature coordinating solvent, tri-n-octylphosphine oxide (TOPO), was used for the synthesis, leading to high-quality QDs that were capped by a monolayer of TOPO molecules. These dots were highly fluorescent (about 60% quantum yields) and monodispersed (about 5% size variations). QD-encoded microbeads were prepared by using 0.5 µm mesoporous microbeads in butanol, and were isolated and purified as reported previously.

A triblock copolymer consisting of a poly-butylacrylate segment, a poly-ethylacrylate segment, and a poly-methacrylic acid segment was purchased from Sigma (St. Louis, Mo.). At a molecular weight of about 100,000 daltons, this polymer contains more than 1000 total monomer units, with a weight distribution of 23% methacrylic acid and 77% combined butyl and ethyl acrylates. For encapsulating QDs, about 25% of the free carboxylic acid groups were derivatized with octylamine (a hydrophobic side chain). Thus, the original polymer dissolved in dimethylformamide (DMF) was reacted with n-octylamine at a polymer/octylamine molar ratio of 1:40, using ethyl-3-dimethyl amino propyl carbodiimide (EDAC, 3-fold excess of n-octylamine) as a cross-linking reagent. The product yields were generally greater than 90% due to the high EDAC coupling efficiency in DMF (determined by a change of the free octylamine band in thin layer chromatography). The reaction mixture was dried with a ratovap (Rotavapor R-3000, Buchi Analytical Inc, Delaware). The resulting oily liquid was precipitated with water, and was rinsed with water 5 times to remove excess EDAC and other by-products. After vacuum drying, the octylamine-grafted polymer was re-suspended in an ethanol/chloroform mixture, and was stored for use.

Surface modification and bioconjugation: Using a 3:1 (v/v) chloroform/ethanol solvent mixture, TOPO-capped quantum dots were encapsulated by the amphiphilic tri-block polymer. A polymer-to-QD ratios of 5 to 10 was used because molecular geometry calculations indicated that at least 4 polymer molecules would be required to completely encapsulate one quantum dot. Indeed, stable encapsulation (e.g., no aggregation) was not achieved at polymer/dot ratios less than 4:1. After vacuum drying, the encapsulated dots were suspended in a polar solvent (aqueous buffer or ethanol), and were purified by gel filtration. Standard procedures were then used to crosslink free carboxylic acid groups (about 100 on each polymer molecule) with amine-containing ligands such as amino-PEGs (Sunbio, Korea), peptides, and antibodies. Briefly, the polymer-coated dots were activated with 1 mM EDAC at pH 6 for 30 min. After purification, the activated dots were reacted with amino-PEG at a QD/PEG molar ratio of 1:50 at pH 8 for 2 hours, generating PEG-linked probes. Alternatively, the activated dots were reacted with PEG at a reduced QD/PEG ratio of 1:6 at pH 8 for 20 min, and then with a tumor-targeting antibody at a QD/antibody molar ratio of 1:15 for 2 hours. The final QD bioconjugates were purified by column filtration or ultracentrifugation at 100,000 g for 30 min. After resuspension in PBS buffer (pH 7), aggregated particles were removed by centrifugation at 6000 g for 10 min.

QD-streptavidin was prepared by using the same cross-linking reagent (1-mM EDAC) and under the same experimental conditions (1:15 QD/strepavidin molar ratio, pH 8, room temperature, and 2 hours) as for QD-antibody conjugates. After purification by column filtration, QD-streptavidin was mixed with biotinylated Tat (or polyarginine) at a QD/peptide molar ratio of 1:20, and was incubated at room temperature in PBS buffer (pH 7) for 30 min with occasional sonication. The product was purified by filtration column chromatography. Conjugation of Tat or polyarginine to QDs was confirmed by using dual-labeled peptides (biotin at one end and an organic dye separate from QD fluorescence at the other end). The peptide-QD conjugate was added to cell culture media to a final concentration of 20 nM, and was incubated at 37° C. from 1 hour to 24 hours.

Fluorescence imaging: In vivo fluorescence imaging was accomplished by using a macro-illumination system (Lightools Research, Encinitas, Calif.), designed specifically for small animal studies. True-color fluorescence images were obtained using dielectric long-pass filters (Chroma Tech, Brottleboro, Vt.) and a digital color camera (Optronics, Magnafire SP, Olympus America, Melville, N.Y.). Wavelength-resolved spectral imaging was carried out by using a spectral imaging system (CRI, Inc., Woburn, Mass.) comprising a optical head that includes a liquid crystal tunable filter (LCTF, with a bandwidth of 20 nm and a scanning wavelength range of 400 to 720 nm), an optical coupler and a cooled, scientific-grade monochrome CCD camera, along with image acquisition and analysis software. The tunable filter was automatically stepped in 10 nm increments from 580 to 700 nm while the camera captured images at each wavelength with constant exposure. Overall acquisition time was about 10 seconds. The 13 resulting TIFF images were loaded into a single data structure in memory, forming a spectral stack with a spectrum at every pixel. With spectral imaging software, small but meaningful spectral differences could be rapidly detected and analyzed.

Autofluorescence spectra and quantum dot spectra were manually selected from the spectral image using the computer mouse to select appropriate regions. Spectral unmixing algorithms (available from CRI, Inc., Woburn, Mass.) were applied to create the unmixed images of "pure" autofluorescence and "pure" quantum dot signal, a procedure that takes about one second on a typical personal computer. When appropriately generated, the autofluorescence image should be uniform in intensity regardless of the presence or absence of quantum-dot signals (as is the case in FIG. 6A through 6D). The identification of valid spectra for unmixing purposes need only be performed initially, as the spectra can be saved in spectral libraries and re-used on additional spectral stacks.

Cells and tissue sections were examined by using an inverted Olympus microscope (IX-70) equipped with a digital color camera (Nikon D1), a broad-band ultraviolet (330-385 nm) light source (100-W mercury lamp), and a long-pass interference filter (DM 400, Chroma Tech, Brattleboro, Vt.). Wavelength-resolved spectra were obtained by using a single-stage spectrometer (SpectraPro 150, Roper Scientific, Trenton, N.J.).

Cell, tissue, and whole-animal studies: Both human breast cancer cells (MDA-MB-231) and PSMA-positive human prostate cancer cells (C4-2) were used for implantation into immuno-compromised Balb/c nude mice. These two cell lines were maintained in RPMI and T media, respectively with 10% fetal bovine serum. Conventional immunohistochemical procedures were used to determine the binding of PSMA Ab-QD conjugate to C4-2 prostate cancer cells, utilizing both PEG-QD (no antibody) and PC-3 cells (no PSMA antigen) as negative controls. For pre-tagging of cancer cells, QDs were linked to a transduction peptide such as HIV Tat or polyarginine as noted above, and were delivered into living cancer cells by incubation at 37° C. After one hour incubation, each cell was found to contain more than one million QDs, and with overnight incubation, essentially all the QDs were localized in the cell nucleus.

Using protocols approved by the Institutional Animal Care and Use Committee of Emory University, about one million tumor cells were injected into 6-8 week old nude mice subcutaneously (Charles River, Wilmington, Mass.). Tumor growth was monitored daily until it reached the acceptable sizes. The mice were divided into 2 groups for passive and active targeting studies. QD bioconjugates were injected into the tail vein, at 0.4 nmole for active targeting or 6.0 nmol (about 15 times more) for passive targeting. The mice were placed under anesthesia by injection of a Ketamine and Xylazine mixture intraperitoneally at a dosage of 95 mg/kg and 5 mg/kg, respectively. In a dark box, illumination was provided by fiberoptic lighting, and a long pass filter was used to reject scattered excitation light and to pass Stokes-shifted QD fluorescence. Fluorescent images were recorded by scientific-grade CCDs. After whole-body imaging, the mice were sacrificed by $CO_2$ overdose. Tumor and major organs were removed and frozen for histological QD uptake and distribution studies. Tissue collections were cryosectioned into 5-10 μm thickness sections, fixed with acetone at 0° C., and examined with an epi-fluorescence microscope (Olympus Axiovert, Melville, N.Y.).

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

Therefore, having thus described the invention, at least the following is claimed:

1. A nanostructure, comprising:
  a quantum dot; and
  a hydrophobic protection structure encapsulating the quantum dot, said hydrophobic protection structure comprising:
    a capping ligand disposed on the surface of the quantum dot, and
    an amphiphilic ABC triblock copolymer, wherein the amphiphilic ABC triblock copolymer includes a plurality of alkyl side chains conjugated thereto, said alkyl side-chains each comprising at least eight carbons (—C-8-) and interacting with the capping ligand, and said amphiphilic ABC triblock copolymer encapsulating the quantum dot having the capping ligand disposed thereon and not extending from the surface of said quantum dot having the capping ligand disposed thereon surface, thereby forming a hydrophobic protection layer encapsulating the quantum dot.

2. The nanostructure of claim 1, wherein the amphiphilic ABC triblock copolymer comprises a poly-butylacrylate segment, a poly-ethylacrylate segment, and a poly-methacrylic acid segment, and the plurality of alkyl side-chains are conjugated to the poly-methacrylic acid segment.

3. The nanostructure of claim 1, wherein the amphiphilic ABC triblock copolymer has a molecular weight of about $10^5$ daltons and comprises about 77 weight percent of the poly-butylacrylate segment and about 23 weight percent of the poly-ethylacrylate segment and the poly-methacrylic acid segment, and wherein the plurality of alkyl side-chains are conjugated to the poly-methacrylic acid segment.

4. The nanostructure of claim 1, wherein the quantum dot is CdTe/CdSe.

5. The nanostructure of claim 1, further comprising a biocompatibility compound substantially disposed on the surface of the amphiphilic ABC triblock copolymer.

6. The nanostructure of claim 5, wherein the bio-compatibility compound is a polyethylene glycol.

7. The nanostructure of claim 5, further comprising a probe substantially disposed on the surface of the hydrophobic protection structure, wherein the probe is an antibody, a polypeptide, a polynucleotide, a drug molecule, an inhibitor compound, or any combination thereof.

8. The nanostructure of claim 5, wherein the probe includes a tumor-targeting ligand.

9. The nanostructure of claim 5, wherein the probe includes a prostate tumor-targeting ligand.

10. The nanostructure of claim 1, wherein the capping ligand comprises tri-octylphosphine oxide.

11. A method of preparing a nanostructure, comprising:
  (i) providing a quantum dot having a capping ligand disposed on the surface thereof; and
  (ii) contacting the quantum dot having a capping ligand disposed on the surface thereof with a composition comprising an amphiphilic ABC triblock copolymer, wherein the amphiphilic ABC triblock copolymer includes a plurality of alkyl side chains conjugated thereto, said alkyl side-chains each comprising at least eight carbons (—C-8-), and said amphiphilic ABC triblock copolymer encapsulating the quantum dot having a capping ligand disposed on the surface thereof and not extending from the surface of said quantum dot having a capping ligand disposed on the surface thereof surface, thereby forming a hydrophobic protection layer encapsulating the quantum dot.

12. The method of claim 11, further comprising attaching a bio-compatibility compound to the hydrophobic protection layer.

13. The method of claim 12, wherein the bio-compatibility compound is a polyethylene glycol.

14. The method of claim 11, further comprising attaching a probe to the hydrophobic protection layer.

15. The method of claim 14, wherein the probe is an antibody, a polypeptide, a polynucleotide, a drug molecule, an inhibitor compound, or any combination thereof.

16. The method of claim 11, wherein the capping ligand comprising tri-octylphosphine oxide, and wherein the amphiphilic ABC triblock copolymer structure comprises a poly-butylacrylate segment, a poly-ethylacrylate segment, and a poly-methacrylic acid segment.

17. The method of claim 16, wherein the amphiphilic ABC triblock copolymer has a molecular weight of about $10^5$ daltons and comprises about 77 weight percent of the poly-butylacrylate segment and about 23 weight percent of the poly-ethylacrylate segment and the poly-methacrylic acid segment, and wherein the plurality of alkyl side-chains are conjugated to the poly-methacrylic acid segment.

* * * * *